(12) United States Patent
Csapo et al.

(10) Patent No.: US 9,375,290 B2
(45) Date of Patent: Jun. 28, 2016

(54) STENTS AND METHOD FOR DENTAL RESTORATION USING SAME

(71) Applicant: Turn Key Dental Academy, Inc., North Royalton, OH (US)

(72) Inventors: Arpad Ferenc Csapo, Westlake, OH (US); Karl Edison Hegyi, Strongsville, OH (US)

(73) Assignee: Turn Key Dental Academy, Inc., North Royalton, OH (US)

( * ) Notice: Subject to any disclaimer, the term of this patent is extended or adjusted under 35 U.S.C. 154(b) by 314 days.

(21) Appl. No.: 14/220,419

(22) Filed: Mar. 20, 2014

(65) Prior Publication Data

US 2014/0205967 A1    Jul. 24, 2014

Related U.S. Application Data

(60) Division of application No. 13/270,864, filed on Oct. 11, 2011, now Pat. No. 8,696,356, which is a continuation-in-part of application No. PCT/US2011/040163, filed on Jun. 13, 2011.

(60) Provisional application No. 61/353,807, filed on Jun. 11, 2010.

(51) Int. Cl.
    *A61C 9/00*    (2006.01)
    *A61C 5/04*    (2006.01)
    *A61C 5/10*    (2006.01)

(52) U.S. Cl.
    CPC .... *A61C 5/04* (2013.01); *A61C 5/10* (2013.01)

(58) Field of Classification Search
    CPC ............... A61C 9/00; A61C 5/04; A61C 5/02
    USPC ........................................ 433/37, 213–217.1
    See application file for complete search history.

(56) References Cited

U.S. PATENT DOCUMENTS

| | | | |
|---|---|---|---|
| 2,391,106 A * | 12/1945 | Saffir | A61C 13/081 264/19 |
| 3,058,216 A * | 10/1962 | Cohen | A61C 5/10 264/162 |
| 3,808,687 A | 5/1974 | Millet | |
| 3,987,545 A | 10/1976 | Kennedy | |
| 4,080,736 A | 3/1978 | Kennedy | |
| 4,129,946 A | 12/1978 | Kennedy | |
| 4,172,323 A | 10/1979 | Orlowski | |
| 4,368,040 A | 1/1983 | Weissman | |
| 4,431,421 A | 2/1984 | Kawahara et al. | |
| 4,473,353 A * | 9/1984 | Greggs | A61C 5/002 433/215 |
| 5,035,615 A * | 7/1991 | Din | A61C 5/125 433/215 |

(Continued)

*Primary Examiner* — Yogesh Patel
(74) *Attorney, Agent, or Firm* — Rankin, Hill & Clark LLP

(57) ABSTRACT

A method for dental restoration that includes disposing a flowable and curable tooth restoration composition into an open cavity of a stent that defines contours of a final design model of a patient's teeth and includes an interproximal contact that has been thinned along an interproximal contact zone but not separated, seating the stent on the patient's teeth such that the flowable and curable tooth restoration composition fills a space between at least one tooth to be restored and the stent, initiating curing of the flowable and curable tooth restoration composition in the stent such that the composition bonds to the at least one tooth to be restored and forms at least one restored tooth and removing the stent from the patient's teeth to expose the at least one restored tooth.

18 Claims, 14 Drawing Sheets

(56) References Cited

U.S. PATENT DOCUMENTS

| | | | | |
|---|---|---|---|---|
| 5,084,978 | A | 2/1992 | McReynolds | |
| 5,192,207 | A * | 3/1993 | Rosellini | A61C 5/00 264/19 |
| 5,332,390 | A | 7/1994 | Rosellini | |
| 5,348,475 | A | 9/1994 | Waknine et al. | |
| 5,775,913 | A | 7/1998 | Updyke et al. | |
| 5,803,737 | A | 9/1998 | Lyalin | |
| 5,975,906 | A | 11/1999 | Knutson | |
| 5,984,682 | A | 11/1999 | Carlson | |
| 6,106,747 | A * | 8/2000 | Wohlwend | A61C 5/10 264/16 |
| 6,299,449 | B1 | 10/2001 | Carlson | |
| 6,361,721 | B1 | 3/2002 | Stern | |
| 6,479,592 | B2 | 11/2002 | Rheinberger et al. | |
| 6,691,764 | B2 | 2/2004 | Embert et al. | |
| 6,769,913 | B2 | 8/2004 | Hurson | |
| 7,217,131 | B2 | 5/2007 | Vuillemot | |
| 7,758,346 | B1 * | 7/2010 | Letcher | A61C 8/0048 433/172 |
| 8,393,897 | B2 * | 3/2013 | Clark | A61C 5/04 433/39 |
| 2004/0053189 | A1 | 3/2004 | Friedman | |
| 2004/0241609 | A1 | 12/2004 | Jia et al. | |
| 2005/0146064 | A1 * | 7/2005 | Fecher | A61C 13/20 264/19 |
| 2006/0160043 | A1 | 7/2006 | Cleary et al. | |
| 2006/0172253 | A1 | 8/2006 | Pumphrey et al. | |
| 2007/0054234 | A1 | 3/2007 | Oxman et al. | |
| 2009/0298006 | A1 | 12/2009 | Schwartz | |
| 2011/0212420 | A1 * | 9/2011 | Vuillemot | A61C 13/0004 433/215 |

* cited by examiner

STENTS AND METHOD FOR DENTAL RESTORATION USING SAME

CROSS-REFERENCE TO RELATED APPLICATIONS

This application is a division of U.S. application Ser. No. 13/270,864, filed Oct. 11, 2011, now U.S. Pat. No. 8,696,356 B2, which application was a continuation-in-part of U.S. Application Ser. No. PCT/US2011/040163, filed Jun. 13, 2011, and claims priority to U.S. Provisional App. Ser. No. 61/353,807, filed Jun. 11, 2010.

BACKGROUND OF INVENTION

1. Field of Invention

The present invention relates generally to stents for use in dental restoration and methods for making and using the same.

2. Description of Related Art

Vuillemot, U.S. Pat. No. 7,217,131 B2, discloses a method for forming a dental restoration that involves: (a) preparing selected teeth to be restored for bonding with a fluid polymer composition; (b) covering teeth which are not to be restored with a polymer release material; (c) fitting a clear polymer composition mold over the teeth to be restored and the teeth not to be restored, which mold provides a closed space to be filled between the teeth to be restored and the mold which defines a shape of the restored teeth, wherein the mold has an inlet port for injection of the fluid polymer composition and an outlet port for removing any excess air and excess fluid polymer resulting from the injection; (d) injection molding the fluid polymer composition into the mold to fill the space in the mold with the covered teeth and the teeth to be restored; (e) curing the fluid polymer composition onto the teeth to be restored in the clear polymer composition mold; and (f) removing the mold from the teeth and the tape from the covered teeth to provide the restored teeth in the patient. The process must be repeated in order to restore teeth that were covered with release tape during the first dental restoration procedure.

The processes disclosed by Vuillemot represent an advance in the dental restoration art. But there is substantial room for improvement. For example, it would be highly desirable to be able to restore a plurality of teeth in a single procedure, including adjacent teeth. Furthermore, it would also be highly desirable to be able to more accurately restore a plurality of teeth in a relatively short period of time in a single procedure.

BRIEF SUMMARY OF THE INVENTION

The present invention provides stents for use in dental restoration and methods for making and using the same. The stents according to the invention and the method of restoring one or more teeth according to the invention make it possible to quickly and accurately restore a plurality of teeth in one procedure, including adjacent teeth.

In one embodiment, a stent is formed by applying a first curable material onto a final design model of a patient's teeth and proximal soft tissues such that the first curable material covers a plurality of teeth including at least one tooth to be restored and contacts the proximal soft tissues facial and lingual to the at least one tooth to be restored. The first curable material is cured on the final design model under pressure to form a cured initial mold. An opening is then formed in the cured initial mold. The opening exposes the at least one tooth to be restored when the cured initial mold is seated on the final design model of the patient's teeth. A second curable material is then applied onto the exposed at least one tooth to be restored and the cured initial mold seated on the final design model of the patient's teeth. The second curable material is cured on the final design model and the cured initial mold under pressure to form the stent having a first portion formed of the first curable material and a second portion formed of the second curable material. The stent is removed from the final design model to expose a mold cavity that defines contours and dimensions of the final design model of the patient's teeth and proximal soft tissues.

In a second embodiment of the invention, a stent is formed by vacuum or positive pressure thermoforming a first sheet of thermoformable material onto a final design model of the patient's teeth and proximal soft tissues. The thermoformed first sheet is trimmed such that it defines a tray that covers a plurality of teeth including at least one tooth to be restored and the proximal soft tissues facial and lingual to the at least one tooth to be restored. A second sheet of thermoformable material is vacuum or positive pressure thermoformed onto the tray and the final design model of the patient's teeth and proximal soft tissues. The thermoformed second sheet is trimmed such that it extends beyond a peripheral edge of the thermoformed first sheet. The thermoformed second sheet is separated from the thermoformed first sheet. A curable material is applied onto the final design model of the patient's teeth and proximal soft tissues and then covered with the thermoformed second sheet. The covered curable material on the final design model is cured under pressure to form the stent having a first portion formed of the curable material and a second portion formed of the thermoformed second sheet. The stent is then removed from the final design model to expose a mold cavity that defines contours and dimensions of the final design model of the patient's teeth and proximal soft tissues.

In a third embodiment of the invention, a stent is formed by applying a first curable material onto a final design model of the patient's teeth and proximal soft tissues. The first curable material covers a plurality of teeth including at least one tooth to be restored and contacts the proximal soft tissues facial and lingual to the at least one tooth to be restored. The first curable material is cured on the final design model under pressure to form a cured initial mold. A sheet of thermoformable material is vacuum or positive pressure thermoformed onto the cured initial mold. The thermoformed sheet is trimmed such that it defines a tray that covers the plurality of teeth including at least one tooth to be restored and the proximal soft tissues facial and lingual to the at least one tooth to be restored. The cured first curable material is separated from the thermoformed sheet and an opening is formed in the first curable material such that when the first curable material is reseated on the final design model of the patient's teeth and soft tissues, the opening surrounds the at least one tooth to be restored and proximal soft tissues facial and lingual thereto. A second curable material is applied onto the final design model of the patient's teeth and proximal soft tissues in the area of the opening and is covered with the thermoformed sheet. The covered second curable material is cured on the final design model under pressure to form the stent having a first portion formed of the second curable material and a second portion formed of the thermoformed sheet. The stent is removed from the final design model to expose a mold cavity that defines contours of the final design model of the patient's teeth and proximal soft tissues.

In accordance with the method of restoring teeth according to the invention, a flowable and curable composite polymer tooth restoration composition is disposed in the stent such that the flowable and curable composite polymer tooth restoration composition is disposed in the impression of the at least one tooth to be restored. It will be appreciated that the degree to which the flowable and curable composite polymer is filled will vary based upon the particular restoration goals, with higher filler content generally leading to restorations that are generally more physically durable. The process has been practiced using highly-filled (herein defined as being >75% solids by weight) flowable and curable composite polymer materials with great success. It is anticipated that flowable and curable composite materials that are not as highly filled will also perform adequately. The stent is seated on the patient's actual teeth such that the flowable and curable composite polymer tooth restoration composition fills a space between the actual at least one tooth to be restored and the impression of the at least one tooth to be restored made from the final design model of a patient's teeth and proximal soft tissues. Curing of the flowable and curable composite polymer tooth restoration composition is initiated in the stent such that the flowable and curable composite polymer restoration composition bonds to the actual at least one tooth to be restored. Curing can conveniently be initiated using light within the wavelength of 400 nm to 500 nm. It will be appreciated that there are many means of initiating cure (e.g., chemical, thermal, radiative), and thus the specific means of initiating cure is not deemed to be critical to the invention. The stent is removed from the patient's actual teeth to expose at least one restored tooth.

The method of the present invention does not require the use of release agents such as flouorpolymer tapes, which are required in the method according to Vuillemot. Furthermore, a plurality of teeth including adjacent teeth can be restored at the same time. This reduces the time and complexity of the restoration process, and improves accuracy.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

BRIEF DESCRIPTION OF THE DRAWING FIGURES

DETAILED DESCRIPTION OF THE INVENTION

Figure 1:
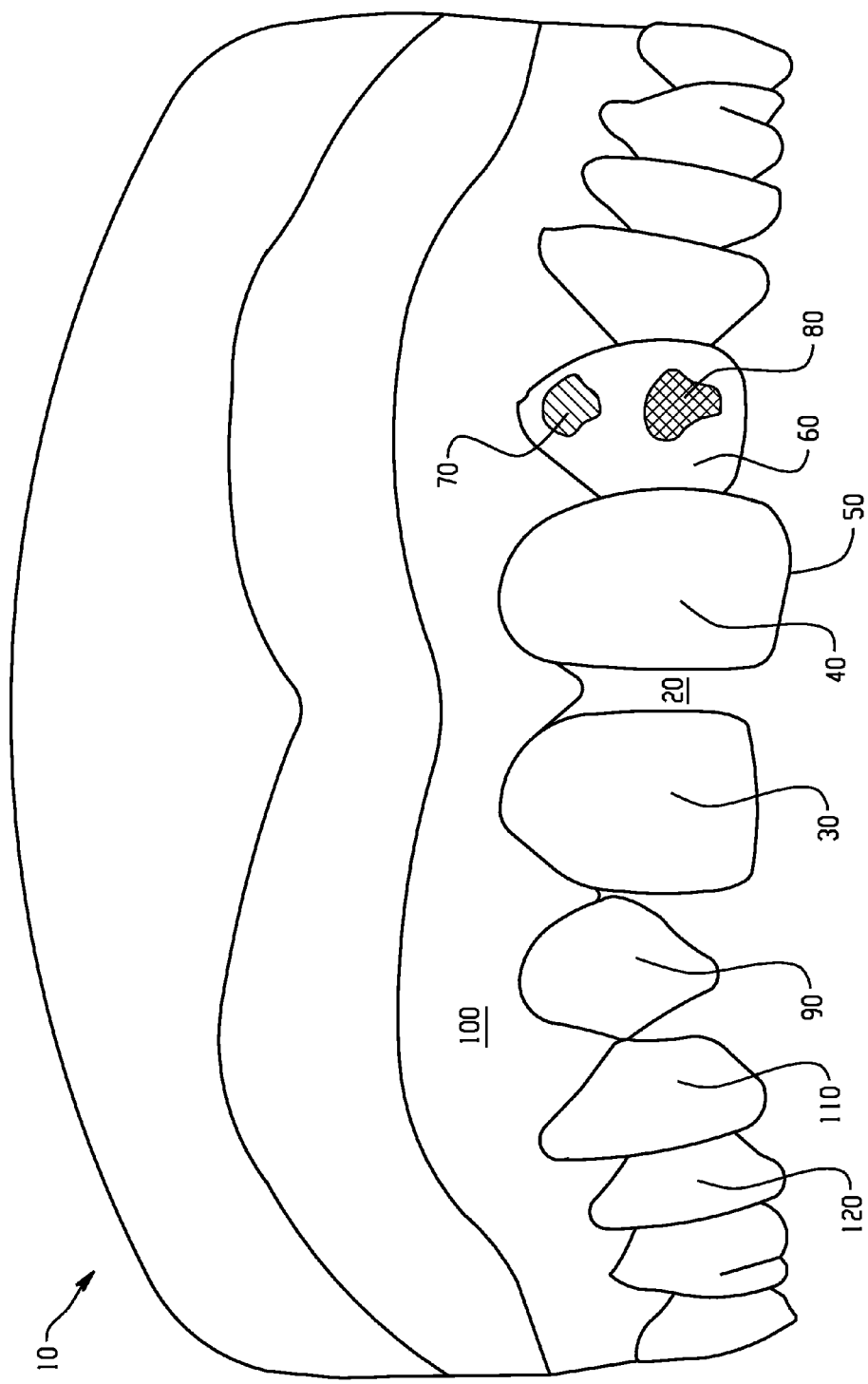
FIG. 1 is a schematic front view of a cast made of a patient's teeth in need of dental restoration.

The present invention allows a patient to address and correct one or multiple problems with a patient's teeth at one time. Throughout the instant specification and in the appended claims unless otherwise indicated, the term "patient's teeth" refers to the patient's teeth as of the time they are treated in accordance with the invention. Thus, the term "patient's teeth" includes the teeth as they existed in their natural state plus any additions or changes that may have occurred to the teeth prior to treatment, whether such changes were unintentional (e.g., teeth that are broken, missing, stained and/or carious) or intentional (e.g., teeth that have previously received treatments such as fillings, crowns, bridges, onlays, or veneers etc. or which have been prepared for such treatments). The method can be utilized to apply dental composite over such prior treatments, or the prior treatments may be removed and replaced with dental composite in accordance with the invention.

The corrections made in accordance with the present invention may serve as the definitive treatment or represent interim treatment that will serve as a template upon which other definitive treatment may be phased over a significant period of time. Throughout the instant specification and in the appended claims, such treatment is referred to as "restorative treatment".

Conventional treatments often require commitments of time and money that prevent patients from moving forward with treatment. Options to phase treatment are desirable because they make treatment acceptable to more patients by allowing them to spread costs over a longer period of time. In addition, shorter visits made possible by phasing may be more comfortable or practical for the patient and dentist. The present invention thus advantageously allows for many restorative issues to be addressed definitively in a single sitting, or allows an improved means of phasing other definitive restorative treatments over an extended period of time. Other means of making interim restorations to allow phasing treatment require more invasive tooth preparation and present problems such as:

1. aesthetic and/or functional compromise of final treatment (especially if treatment is phased segmentally);
2. complications from maintaining interim restorations on prepared teeth over long periods of time; and
3. increased expenses.

Whenever restorative treatment is performed in accordance with the invention, the goal should be to provide restorations that are functionally, aesthetically, and structurally ideal for the patient. Without each, patient satisfaction and the long-term durability of restorative treatment is not predictable. A Stable Biomechanical Foundation is intended to help achieve these objectives by uniting biomechanical harmony with restorative and aesthetic wants and needs. A Stable Biomechanical Foundation is achieved when interocclusal relationships are in harmony with masticatory muscle function, together with healthy or well-adapted temporomandibular joint ("TMJ") function, at the final treatment vertical dimension of occlusion. It requires that maximum intercuspation occurs with equal intensity, simultaneous contact of all teeth with both condyles in their physiologically seated positions. It also requires an anterior guidance that allows disclusion of the posterior teeth and one that is in harmony with the envelope of function. It will be appreciated that in some restorations, functional correction is not needed or is not an objective of the treatment.

To assure compatibility with restorative and aesthetic objectives, one should consider the correct vertical dimension of occlusion when creating a Stable Biomechanical Foundation. The vertical dimension chosen impacts upon four important clinical factors:
1. the invasiveness of reductive reshaping or restorative treatment necessary to develop the foundation;
2. the horizontal, anterior—posterior relationship of upper incisor lingual contours to lower incisor edges (also referred to as the "available envelope of function");
3. the vertical interocclusal or interincisal room available for aesthetic and/or restorative treatments; and
4. treatment aesthetics.

In most situations, biomechanical harmony is possible over a range of vertical dimensions. However, within this range, the appropriate vertical dimension is the one that allows the least invasive treatment while also being consistent with patient restorative and aesthetic wants and needs.

A Stable Biomechanical Foundation may be initially achieved with preparation of teeth and placement of interim restorations. However, often there are advantages to developing this foundation prior to these being done. Advantages include:
1. greater treatment acceptance (because many patients with jaw pain are not interested in aesthetic or restorative treatment until the development of biomechanical harmony eliminates this pain);
2. an easier and more predictable process of functional and aesthetic design and treatment; and
3. the possibility of many treatment-phasing options (because the final vertical dimension of occlusion has been established).

Treatment options to create a Stable Biomechanical Foundation include orthognathic surgery, orthodontics, additive reshaping (with direct or laboratory fabricated restorations), and reductive reshaping. The option(s) that most conservatively achieves biomechanical harmony, and is also consistent with patient restorative and aesthetic wants and needs, should be utilized.

The present invention provides a process that can be used when the requirements of a Stable Biomechanical Foundation can be achieved with additive reshaping or when the requirements of a Stable Biomechanical Foundation can be achieved with a combination of additive reshaping and reductive reshaping alone. The process according to the present invention allows for:
1. a less invasive treatment (particularly if only additive reshaping is required and such additive reshaping does not require tooth preparation);
2. greater control over the treatment vertical dimension of occlusion;
3. achievement of the goals of a Stable Biomechanical Foundation in a greater variety of situations; and
4. the opportunity for both functional and aesthetic corrections.

When developing a Stable Biomechanical Foundation, the proper blend of reductive and additive reshaping should be decided by overall patient wants and needs. If the patient has only biomechanical needs, the blend of reductive and additive reshaping that allows the most conservative treatment should be chosen. When treatment of this nature is indicated on structurally intact and aesthetically acceptable teeth (which it frequently is), reshaping is usually dominantly a reductive process. Additive reshaping typically involves adding minimal amounts of bonded composite to create occlusal stops in such cases. However, there are clinical situations where additive reshaping is the dominant need in developing a Stable Biomechanical Foundation. This occurs when any of the following conditions exist:
1. the vertical dimension of occlusion should be maintained at or opened from the vertical dimension of first occlusal contact when the condyles are physiologically seated;
2. significant addition to existing tooth contours is required for ideal functional design; or
3. significant addition to existing tooth contours is required for ideal aesthetic design.

These conditions exist most frequently when there are patient restorative or aesthetic wants and needs independent of biomechanical needs.

When restorations are required to improve function or aesthetics, resulting tooth contours and dimensions will virtually always differ from those prior to treatment. This will involve some combination of addition to (additive reshaping) and reduction of (reductive reshaping) pre-treatment tooth contours and dimensions. With restorative and aesthetic treatment, these changes are usually dominantly additive. Reductive changes are usually limited to portions of teeth that are rotated, over erupted, malpositioned, or interfering with the chewing cycle. Regardless of the amount of each required, the combined additive and reductive reshaping should ideally create a Stable Biomechanical Foundation. However, they can also lead to development of an ideal functional and aesthetic design for future restorations. If they do, this result could serve as interim restorations that will be a template for definitive restorations.

Use of additive and reductive reshaping in this manner (i.e., to develop ideal functional and aesthetic interim restorations) is one object of the process according to the invention. In this process, the addition is done with the laboratory assisted, direct addition of composite to existing teeth as further described below. However, reduction does not involve conventional final or interim restoration tooth preparation. Rather, it is limited to removal of tooth structure that:
1. is outside of planned definitive restoration contour and dimension (i.e. biomechanically or aesthetically excessive tooth structure);
2. will compromise restoration structural quality (i.e. defective tooth structure such as carious or poorly mineralized dentin or enamel);
3. will compromise restoration aesthetic quality (i.e. defective tooth structure such as discolored tooth structure); and/or
4. must be removed in teeth opposing restored teeth to accommodate re additions made to the restored teeth (i.e. accommodating excessive tooth structure)

When complex restorative treatment is indicated, and the restorations represent interim treatment, advantages of the process according to the invention include:

1. the ability of the patient to live with planned functional and aesthetic changes before committing to definitive treatment (once tooth preparations are made);
2. an easier and more economical means of creating and maintaining long-term interim restorations;
3. an easier process of final tooth preparation (because final tooth contour and dimension is established prior to tooth preparation); and
4. the ability to making complex aesthetic and restorative treatment possible for many more patients Material choice and technique for additive reshaping depend upon the quantity and objective of the addition. As previously described, when it is done to restore biomechanical harmony to structurally intact, aesthetically acceptable teeth, it usually involves the direct application of a light-curable composite polymer tooth restoration composition. Typically this is done with a conventional, non-flowable, high viscosity composite bonded to enamel. However, when specific clinical situations exist, adding composite this way may be impractical or impossible. Some of these situations include:
1. a large number of teeth requiring addition;
2. a large quantity of addition being required;
3. teeth that are difficult to access or isolate; and
4. a desire for aesthetic changes from the additions.

When any of these situations exist, the ability to design the additions indirectly and then duplicate them in the mouth with a durable and aesthetic restorative material is of tremendous value. This is what the process according to the invention facilitates. And, it accomplishes this task in a way that is similar to a technique used to make conventional interim restorations. In this commonly used technique, a mold (made of alginate, putty silicone, or some other elastomeric material) of the planned tooth design is first made (usually from a wax-up). Then, after tooth preparation, the mold is filled with an interim restorative material and carried to the mouth to make an interim duplication of the planned design. Although similar, the process according to the invention differs from conventional techniques in several ways including, but not limited to:
1. the design of the stent used to bring the restorative material to the patient's teeth;
2. the properties of the restorative material used in the stent;
3. the requirement of micromechanical or chemical bonding between the restorative material and tooth;
4. the removal of tooth structure being limited as previously described in this section; and
5. the design of the wax-up or restorative plan.

One important aspect to the success of the restorative process according to the invention is the choice of restorative material used. Once completed, each restoration will be some blend of this material and existing tooth structure. It is important that the material can be applied to the tooth and can withstand occlusal forces in a wide variety of thicknesses and dimensions. This allows conservation of tooth structure and makes possible additions ranging from very small (e.g. a cusp tip) to very large (e.g. complete occlusal onlays). Although there is ample room for improvement (i.e., subsequent development of materials), there are a few highly-filled flowable composite polymer tooth restoration compositions available on the market that meet the requirements of the present process.

The term "flowable and curable composite polymer tooth restorative composition" as used herein thus refers to a composite dental material that can be placed into a stent, has sufficient fluidity to flow into and fill the space(s) between the patient's teeth to be restored and the contours and dimensions defined by the stent without distorting the stent, and that can be cured to harden the material. In some instances, the flowable and curable composite polymer tooth restorative composition will be a highly filled (>75% solids by weight) composite resin. The material is preferably curable by exposure to light. However compositions that are cured by other means (e.g., chemical or other radiation) are within the scope of the invention. Most preferably, the material is cured with visible light of about 400 nm to about 500 nm, or more preferably from about 450 nm to about 480 nm.

As noted, another important key to the success of the process is the design of the stent. As a combined result of this stent, flowable composite polymeric tooth restoration composition, proper bonding technique, and attention to biomechanical factors, it is possible to make an accurate, detailed, and durable duplication of virtually any restorative design. The results can also be highly aesthetic. Because of the preservation of existing tooth structure, each restoration is also created with an absolute minimum removal of tooth structure.

As noted above, the dental restoration process according to the invention involves the use of additive and, optionally (depending upon the particular case), reductive reshaping to create aesthetically and functionally ideal restorations. Additive reshaping involves selectively applying and curing a light-curable composite polymer tooth restoration composition on one or more teeth to be restored. Reductive reshaping involves selectively removing tooth material prior to the application and curing of the flowable and curable composite polymer tooth restoration composition on one or more teeth to be restored. Additive reshaping is involved in all cases and is typically the dominant part of treatment. Reductive reshaping may be optional depending upon the particular patient's needs and desires. The amount of reduction necessary may determine whether or not the process is the best treatment choice. Even though the process according to the invention requires the least amount of tooth reduction or preparation of any restorative option, reductive needs may make other restorative or non-restorative options more logical. In addition, it is the amount and type of reduction that most affect the laboratory and clinical procedures necessary for each case.

The following are the primary indications for reductive reshaping or tooth preparation related to the process:
1. Tooth architecture that needs to be removed prior to stent design and treatment in order to close the vertical dimension to the appropriate vertical dimension for a Stable Biomechanical Foundation creation. Tooth architecture requiring reduction for this purpose is hereafter referred to as "biomechanically excessive tooth structure";
2. Tooth architecture that is structurally or aesthetically unacceptable. Tooth architecture that is structurally or aesthetically unacceptable is hereafter referred to as "defective tooth structure". Examples of defective tooth structure include discolored, hypo-calcified, or carious tooth structure;
3. Tooth architecture outside ideal aesthetic form. Tooth architectures that are outside ideal aesthetic contour or dimension is hereafter referred to as "aesthetically excessive tooth structure". Examples of aesthetically excessive tooth structure include labially rotated or super-erupted incisors; and
4. Tooth architecture that requires reduction to accommodate aesthetic or functional additions made in the opposing arch. Tooth architecture that requires reduction for either of these purposes is hereafter referred to as "accommodating excessive tooth structure". Examples of accommodating excessive tooth structure include the lingual of upper incisors when lower incisors are lengthened and the occlusal surfaces of lower posterior teeth when upper posterior teeth are lengthened.

In addition to the four primary indications, there are other situations where tooth reduction facilitates an easier and better treatment. One such situation is overlapping anterior teeth. Overlapping anterior teeth typically have enlarged and irregular interproximal contacts that are difficult to separate and refine after composite application (and are also aesthetically and hygienically unacceptable).

Typically, this problem is resolved with the removal of aesthetically excessive tooth structure (as described in the Class III of the process disclosed below). This typically results in an opened interproximal contact. However, there are times that removal of aesthetically excessive tooth structure does not result in an open contact. If it does not, the lab technician opens the contacts on the casts and makes a duplicate cast of the open contacts. The open contacts are then waxed for ideal aesthetics and hygiene as explained below. At the treatment appointment, after aesthetically excessive tooth structure and defective tooth structure are removed, the dentist can visually reference the cast of the opened contacts to assure proper reduction. As an alternative method of communicating the opening of contacts, a reduction guide can be made from a thin clear vacuum or positive pressure thermoformed material applied to the cast prior to opening the contact on the cast. The defective contact is then opened as needed through the overlying thermoformed material and cast simultaneously. The thermoformed material is then removed from the cast and trimmed so that it can be inserted over the patient's teeth. The dentist duplicates what was reduced on the cast by removing the tooth structure through the opening on the reduction guide that was created when the contact was opened on the cast. Depending on the amount of opening required, a diamond disk, tapered carbide bur, or diamond may be used. Whether for this, or any other situation, if additional removal of tooth structure results in a better treatment result, reduce the least amount possible, and proceed with the appropriate treatment class protocol. Typically, only tooth enamel is removed. Dentin is not removed in most cases.

The first indication for reductive reshaping with the process according to the invention occurs prior to restoration design, stent fabrication and treatment. This is for developing a Stable Biomechanical Foundation, which assures the most favorable distribution of forces on the restoration—as well as all other components of the masticatory system. If a patient has an acceptable Functional Occlusion and there is no need to change the vertical dimension, it is not necessary to alter functional occlusal relationships as a part of this invention. However, when patients can benefit from improved functional occlusal relationships or require an altered vertical dimension, a Stable Biomechanical Foundation should be developed prior to, or as a result of, treatment.

The first step in developing a Stable Biomechanical Foundation is choosing the treatment vertical dimension. The proper vertical dimension should consider the patient's final functional, restorative, and aesthetic wants and needs. Most frequently this requires closing from the vertical dimension of first tooth contact when the condyles are seated. If it does, reductive reshaping of biomechanically excessive tooth structure is used to achieve this vertical dimension. If all teeth are not in contact after reductive reshaping, additive reshaping is used to establish equal intensity simultaneous contact of all teeth at this vertical dimension.

When reductive and additive reshaping are completed for this purpose, new impressions and a facebow registration are taken, and casts are mounted in maximum intercuspation. Design of the restored teeth and stent may now begin. Note: if the Functional Occlusion or vertical dimension is not altered, casts should still be facebow mounted in maximum intercuspation.

If treatment vertical dimension is to be maintained at or opened from first tooth contact, Stable Biomechanical Foundation development is a purely additive process. In either of these cases, the process may be used to apply these additions and develop the Stable Biomechanical Foundation. However, as noted earlier, when there are only a few, small additions necessary, it is usually done with conventional direct methods.

There are four general classifications of dental restorations that can be accomplished using the process. Each is separately discussed below.

Class I restorations involve addition for aesthetic and/or functional improvement and require no tooth reduction. There is no existing tooth structure outside ideal contour or dimension (i.e., no aesthetically excessive tooth structure) and there is no aesthetically or structurally defective tooth structure (i.e., no defective tooth structure). Also, there is no need to reduce opposing teeth to functionally accommodate the additions (i.e., no accommodating excessive tooth structure). In Class I restorations, the design is carried out for aesthetics and function on facebow-mounted casts. One may perform an aesthetic preview, refine the wax-up of the cast made from the patient's teeth and proximal soft tissue, and then fabricate the stent as described below.

An aesthetic preview involves the temporary application of material (typically an interim restoration material) over teeth requiring restoration, prior to or at the time of treatment—typically using a stent to carry the material to the teeth. It is a tool that may be used to confirm and communicate various aesthetic (and functional) qualities of planned restorations. Although its use is optional, prior to treatment, it allows the patient and dentist to view, and if necessary modify, such aesthetic qualities as restoration contours and dimensions prior to actual treatment. At the time of treatment, the aesthetic preview may serve as a guide for tooth reduction (e.g. confirming if adequate defective stained tooth structure has been removed to allow an acceptable shade once restorative material is applied or to help communicate needed reduction requirements when interproximal contacts are to be opened prior to restorative material application).

Class II restorations involve addition for aesthetic and/or functional improvement with no aesthetically excessive tooth structure or accommodating excessive tooth structure reductive needs. However, Class II restorations require reduction to remove structurally unacceptable tooth structure (defective tooth structure). One should design and refine the wax-up as in a Class I restoration without consideration of reductive changes and fabricate the stent as described below. At the time of restoration, it will be necessary to remove corresponding defective tooth structure from the patient's actual teeth and aesthetically preview to confirm adequate tooth removal for proper post-curing shading. When adequate reduction is confirmed, one can proceed with the restoration as described herein.

Class III restorations require addition for aesthetic and/or functional improvement with no accommodating excessive tooth structure reductive needs. However there is tooth structure outside ideal aesthetic form that requires reduction (i.e., there is aesthetically excessive tooth structure). There may or may not also be structurally unacceptable tooth structure (i.e., defective tooth structure) requiring removal. One must design all additions for ideal aesthetics and function on facebow-mounted casts and, if necessary, do aesthetic previews. One should not remove aesthetically excessive tooth structure from casts at this time. When the additive design is aesthetically confirmed, duplicate master casts must be obtained. It is important that all additions are complete prior to duplication. One can fabricate vacuum or positive pressure thermo-formed shells over the duplicate casts, and relieve aesthetically excessive tooth structure on duplicate casts through shells. The modified shells will serve as reduction guides. If reduction will be into dentin, it may be necessary to reduce the cast beyond aesthetically excessive tooth structure to allow final restorative material to cover exposed dentin. Next, use reduction guide to relieve the master cast. Refine functional/aesthetic design on the master cast and, if further reduction is necessary, relieve the master cast and reduction guide as needed. It should be noted that if properly reduced, any areas of reduction that will result in exposed dentin should be covered with wax when wax-up is finished. The stent can now be fabricated as explained below. Reductive reshaping of the patient's aesthetically excessive tooth structure is performed prior to addition of the flowable and curable dental composite using the reduction guide. If present, remove defective tooth structure and aesthetically preview to confirm adequate tooth removal for proper shading. The process can then be completed using the stent.

And, Class IV restorations involve addition for aesthetic and/or functional improvement that requires a reduction of opposing teeth to functionally accommodate these additions (i.e., accommodating excessive tooth structure). There may or may not also be aesthetically excessive tooth structure and/or defective tooth structure reductive needs. In such instances, one should design all additions for ideal aesthetics and function on facebow-mounted master casts and, if necessary, do an aesthetic preview. When additions are aesthetically confirmed, one should duplicate the master cast and facebow mount. As in Class III cases, if aesthetically excessive tooth structure exists, it is preferably that one fabricate thin thermo-formed shells over duplicate casts, and relieve aesthetically excessive tooth structure on duplicate casts through shell. Next, reduce accommodating excessive tooth structure on duplicate casts to confirm that required reduction is not excessive and that ideal function is achievable with planned additions (i.e. confirm that tooth reduction and function resulting from the additive design will be clinically acceptable). If required accommodating excessive tooth structure reduction and resulting function are acceptable with current additive wax-up, use reduction guide to relieve aesthetically excessive tooth structure from master cast, refine wax-up and fabricate the stent on master casts. One should not remove accommodating excessive tooth structure from master casts as in Class III restorations. If an acceptable combination of addition and accommodating excessive tooth structure is not found with wax-up modification, a different restorative option will be necessary. At the time of restoration fabrication, if present, remove patient's aesthetically excessive tooth structure using confirmed reduction guide. If also present, remove patient's defective tooth structure, and aesthetically preview to confirm adequate removal for proper shade. With aesthetically excessive tooth structure and defective tooth structure removed (if present), apply additive composite using the stent. After composite is applied and cured, reductively reshape tooth structure (i.e. remove accommodating excessive tooth structure) in patient's mouth to ideal function. Finish and polish restorations. It should be noted that if dentin is exposed from accommodating excessive tooth structure removal that requires coverage for sensitivity or to increase wear resistance, inlay composite into exposed dentin.

As noted above, an object of the present invention is to improve a patient's current dental condition, aesthetics, and/or function. The current condition, or wants or needs, described by the patient are referred to as the chief complaint and include aesthetic and functional conditions. Current aesthetic or functional condition may present as one or more of the following: worn tooth surfaces (resulting from mechanical or chemical attrition); fractured teeth; decayed teeth; discolored or stained teeth; teeth which are too small for the arches and therefore have excess space between them; mal-positioned or mal-aligned teeth, teeth which interfere with physiologic (functional) or non-physiologic (parafunctional) movement of the mandible.

Therefore, the desired changes, or restoration of the teeth can be as follows: re-addition of worn surface (which may involve many teeth, and allows the option of "opening the bite"); repair and restoration of fractured teeth; repair and restoration of decayed teeth; covering up of unsightly stains or discolorations; widening of teeth to close spaces or gaps; and additive or subtractive reshaping to improve symmetry, alignment (masking of malposed teeth-giving impression of "instant orthodontics"), and/or function.

Casts should be obtained by taking extremely high-quality impressions of the patient's teeth and proximal soft tissues and then using the impressions and a suitable dental stone material to obtain casts that reflect the current condition of the patient's teeth. In some cases, the cast of the patient's teeth is made after tooth material has been removed by the dentist. Preferably, the impression made that captures the current condition and which is used to create the cast model, is made of polyether or vinyl polysiloxane and captures both hard and soft tissues of the patient's mouth with great accuracy and detail. Preferably, the plaster model comprises a Type 4 die stone. Preferably, the model is accurately mounted on a fully or semi-adjustable articulator with a face bow registration reproducing the patient's most physiologic interocclusal relationship and arc of closure, and demonstrates the chief complaint, which can then be studied carefully.

It will be appreciated that if only one arch is to be restored, only the restored arch needs to have a cast made with these impression materials and stone types. A cast of the non-restored arch may be made using other impression materials and dental stones. It will also be appreciated that the stent needs to be sufficiently large to be able to be accurately seated on the patient's teeth to be restored and proximal teeth/soft tissues, but may not necessarily span all of the patient's upper or lower teeth (i.e., the stent can cover less than the entire arch of upper or lower teeth, provided it positively seats on the patient's teeth to be restored).

As noted, restorations according to the invention require addition to and sometimes reduction of existing tooth structure. Existing undesirable characteristics of the teeth include some combination of defects and deficiencies. These defects and deficiencies may be of existing tooth structural, aesthetic, or functional qualities. Defects may impact on patient function, aesthetics, comfort, or oral health and include, for example:

1. Tooth architecture that is structurally or aesthetically unacceptable. Tooth architecture that is structurally or aesthetically unacceptable is hereafter referred to as defective tooth structure. Examples of defective tooth structure include discolored, hypo-calcified, or carious tooth structure;
2. Tooth architecture outside ideal aesthetic form. Tooth architecture that is outside ideal aesthetic contour or dimension is hereafter referred to as aesthetically excessive tooth structure. Examples of aesthetically excessive tooth structure include labially rotated or super-erupted incisors; and 3. Tooth architecture that needs to be removed prior to design and treatment in order to close vertical dimension and create a Stable Biomechanical Foundation. Tooth architecture requiring reduction for this purpose is hereafter referred to as biomechanically excessive tooth structure.

Deficiencies represent an insufficiency or inadequacy of tooth structure and may impact on patient function, aesthetics, comfort, or oral health and include, for example:

1. Worn teeth;
2. Fractured teeth;
3. Congenitally undersized or undercontoured teeth; and
4. Spaces (diastemas).

Defective tooth structure is removed prior to or at the time of tooth restoration. Deficiencies are added to at the time of restoration.

In order to begin the process, one must first make impressions of the patient's existing or pre-restored teeth. The impressions must capture all tooth details as accurately as those for indirect crowns or onlays. However, for the process according to the invention it is equally important to accurately capture all details of the soft tissues around the teeth. Both are absolutely necessary for the waxing techniques that are explained in further detail below.

To date, although digital impression and digital dental cast fabrication and modeling techniques (e.g., 3D CAD-CAM) seem appealing, such methods do not yet produce the level of tooth and soft tissue detail desired for the process. When the accuracy of such technologies improves, and when cost and efficiency factors are also favorable, digital impression/cast and modeling techniques will likely be of choice for the process. Until that time, either a vinyl polysiloxane or polyether impression material should generally be used. Both materials offer the combination of flowability and strength needed to capture important details and yet not tear when the impression is removed from critical undercuts (such as areas under interproximal contacts that are not filled with the interdental papilla—also known as "dark triangles"). While both impression materials make excellent impressions, polyether's hydrophilic qualities make it the material of choice when moisture control is difficult.

If handled properly, alginates have adequate flowability and accuracy, but they are not very strong. If there are no details that are likely to tear from the impression (such as dark triangles) alginates may be used, but must be poured immediately and should be mixed in two viscosities. A "thin" mix should be made and syringed around the teeth, with a standard viscosity alginate placed in the impression tray. Regardless of impression material used, it is recommended that a rigid custom impression tray or a modified stock tray be used that allows a uniform impression material thickness.

It is also recommended that the impression be poured with a Type 4 Die Stone in order to obtain very accurate casts of the patient's teeth. Prior to designing the restorations, in most cases these casts should be mounted using a facebow and a bite registration with the condyles physiologically seated (in CR).

FIG. 1 is a schematic front view of a cast 10 made of a patient's teeth in need of dental restoration. The cast 10 was poured from Type 4 dental stone using an impression taken of the patient's teeth as described above. There is a diastema 20 between the patient's right central incisor (right front tooth) 30 and the patient's left central incisor (left front tooth) 40. The left central incisor 40 is supererupted (i.e., a portion of the tooth extends below an aesthetically appropriate end line generally defined by the end line of the right central incisor 30), and thus includes excess tooth structure 50 that needs to be removed. The left lateral incisor 60 includes an area of carious tooth structure 70 and an area of staining 80. The right lateral incisor 90 is undersized and is functionally and aesthetically deficient. The cast 10 accurately records the patient's soft tissues 100 proximal to the teeth. Portions of the right canine/eye tooth 110 and right first premolar 120 are aesthetically and functionally deficient, and would benefit from the addition of dental composite. All of the aforementioned defects and deficiencies in the patient's teeth (both biomechanical and aesthetic) can be treated and corrected (i.e., "restored") in accordance with the method of the invention in one treatment session.

Figure 2:
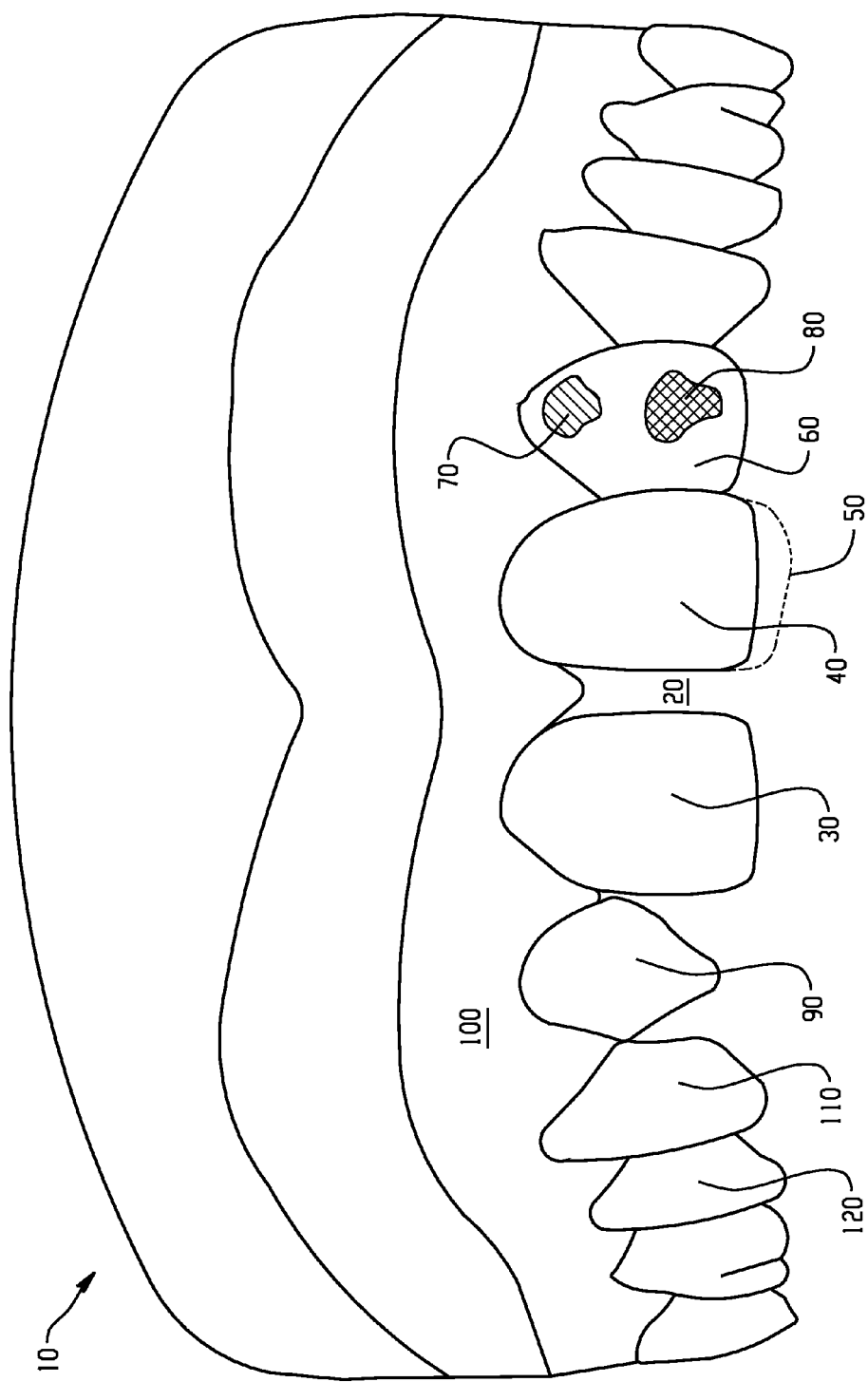
FIG. 2 shows the cast of FIG. 1 after removal of excess tooth structure.

Most tooth reduction with this invention is done prior to making casts (biomechanically excessive tooth structure) or at the time of restoration (defective tooth structure) and do not require modification of the master casts. However, two situations that require modification of the casts (reduction) prior to treatment are aesthetically excessive tooth structure and enlarged, irregular interproximal contacts (typically from overlapping anterior teeth). FIG. 2 shows the cast 10 of FIG. 1 after removal of excess tooth structure 50 from the left central incisor 40. It should be noted that the carious tooth structure 70 and the staining 80 on the left lateral incisor 60 has not been removed. In view of the considerations previously described and in view of the patient's needs, the least amount of material necessary to accomplish the end result is removed from the casts. It will be appreciated that in some cases, no material will need to be removed from the casts at all.

Once the required material has been removed from the casts, wax must be applied to the casts (or modified casts must be produced using digital CAD-CAM technology). Before describing waxing techniques for interproximal contacts, terms for three anatomic areas need to be defined. The waxing details described herein are limited to these three areas. The first is interproximal contact, which is the area between adjacent teeth that are actually touching each other. This area is typically some variation of a line or oval in shape. The second term is interproximal contact zone, which is the tooth structure that contours from the facial and lingual tooth surfaces into the interproximal contact. The contact zone typically extends one to three millimeters from the contact. Its size and shape have an important influence on the perceived shape and contour of the entire tooth. The final term is interproximal emergence area, which is the area between the most apical extent of the interproximal contact and the interdental papilla. It is this area where the interproximal contact and soft tissues are in closest proximity.

For a dentist to create high quality interproximal contacts and contact zones, there are important differences between a wax-up for the process according to the invention and a conventional diagnostic wax-up. These differences involve not only design of the interproximal contact and contact zone, but also the interproximal emergence area. If the following steps are followed, separating and refining contacts is an easy task for the dentist (and patient), and the resulting contacts and contact zones are hygienic and aesthetic. If they are not, this task can be very time consuming and unpleasant, and both contact and contact zone qualities are compromised.

The details of interproximal waxing techniques primarily depend upon the additive changes needed in the interproximal contact and contact zones. The following are possible objectives of these additive changes and the waxing protocols for each:

Addition where open interproximal contacts require closing (diastema closure)

Addition where only the contact zone requires modification

Addition where the existing interproximal contact requires gingival extension ("Dark Triangle" Closure)

Addition where the existing interproximal contact requires incisal or occlusal extension (tooth lengthening)

Addition where the existing interproximal contact and contact zones are not hygienically or aesthetically acceptable and both require modification (overlapping anterior teeth)

When addition is needed to close open interproximal contacts (i.e., diastema closure), the added composite itself will constitute the interproximal contact. It is thus critical that the wax (and therefore composite) making up the contact be extremely thin along the contact. This is accomplished by first contouring the contacts and contact zones to ideal aesthetics and function. The wax-up is then thinned along the contact with an extremely thin blade (e.g., scalpel or knife) The interproximal contact should be thinned to just before the contact is opened.

As the wax-up approaches the gingival margin, the interproximal contact must begin to open and blend into existing tooth structure. The distance from the gingival margin to where this begins depends on the level of the interproximal bone. If an interproximal contact is created 4-5 mm from the boney crest between two natural teeth, a papilla will develop and completely fill the embrasure nearly 100% of the time. Therefore, the interproximal contact should begin to open 4-5 mm from the boney crest. To determine exactly where this is, it is necessary to sound to the boney crest in the interproximal emergence area. In the case of an existing diastema, this is typically 1-1.5 mm from the existing healthy interproximal gingival margin. If this protocol is followed, there will be a small dark triangle at the time of restoration that will close within six months.

The relationship between added wax and existing soft tissues is critical whenever additions approach the gingival margin. An absolute rule is that no wax should extend onto or over the soft tissues of the cast. The wax must end precisely at or short of the soft tissues. This applies whether the addition is in the interproximal area or any other portion of the tooth. If these procedures are followed, separation and refinement of contacts will be an easy process if the finishing techniques described below are followed.

Often times, even when existing interproximal contacts are acceptable, the contact zones require modification. This is common when addition is needed on facial or lingual tooth surfaces (for aesthetic or functional purposes). When it is, addition will also be needed to the facial and/or lingual contact zones, but extension (incisal/occlusal or gingival) of the contact is not needed. The key to modifying the interproximal zone in this situation is to be certain that wax (and therefore the restoration) does not add thickness to the existing contacts. Simply wax the contact zone to ideal contour and dimension, then use an ultra-thin blade (as described above) to reduce the wax along the contact down to the cast. If this protocol is followed, there is no contact separation required (except for any bonding resin in the contact), and finishing is an easy process.

If "dark triangles" exist, the first decision to be made is whether or not they should be closed. Not all patients need or want these spaces closed—especially if they are small or not visible when smiling. If they should be closed, first use the methods described above for modifying the contact zone. Next, use the methods described above for closing diastemas to extend the contact into the dark triangles. As with diastema closure techniques, the interproximal bone level should determine the vertical extension of the contact, and wax must not extend onto any soft tissue portion of the cast. If this is followed, only areas of contact extension should require separation.

There are instances in which addition is required because existing interproximal contact require incisal or occlusal extension (tooth lengthening) for aesthetic or functional reasons. If they do, they may also require extension of the interproximal contacts. The procedures for this addition are similar to those used to close dark triangles. The differences involve the direction of extension and what determines the amount of extension. With dark triangle closure, the interproximal bone determines the vertical extension of the contact. With incisal or occlusal extension, aesthetics and function determine the vertical extension. Once again, if this protocol is followed, only areas of contact extension should require separation.

There are also instances in which addition is required because existing interproximal contact and contact zones are not hygienically or aesthetically acceptable and both require modification (e.g., overlapping anterior teeth). When overlapping anterior teeth produce interproximal contacts and contact zones that are hygienically and aesthetically unacceptable, reduction and addition will be required for both the contact and contact zone. Following the guidelines set forth herein typically results the interproximal contact being opened. If it does, one should follow the reduction protocols described herein and the waxing protocols described herein.

However, if removal of aesthetically excessive tooth structure alone does not result in an open contact, additional reduction will be necessary. The contact should be opened on the cast as little as possible to allow development of an aesthetically and hygienically ideal contact. Then, follow the waxing protocols as herein described for a functionally and aesthetically ideal contact that is easily finished.

It is important that the contact be opened at least as much in the patient's mouth as on the cast. This can be assured by making a duplicate cast of the opened contacts prior to waxing. At the treatment appointment, after aesthetically excessive tooth structure and defective tooth structure are removed, the dentist can visually reference the reduced cast to assure proper reduction. Depending on the amount of opening required, a diamond disk, tapered carbide bur, or diamond may be used.

Although waxing margins on facial and lingual tooth surfaces is separate from interproximal contact waxing, there are similarities in the two waxing techniques. Frequently, the cervical extension of the restoration (and therefore the wax-up) does not approach the gingival margin and simply blends into existing tooth structure. However, more often it extends completely to the gingival margin. If it does, the same rule that guides waxing margins in the interproximal emergence area should be observed. This rule is that added wax should never extend onto or over gingival tissues of the cast. When additions extend to the gingival margin, the wax-up should be meticulously refined under magnification with an ultra-thin wax-carving instrument (such as a #25 scalpel blade) to assure that wax ends exactly at or short of gingival tissues. If wax extends onto the gingiva, restoration finishing will be a more time consuming and potentially harmful process, requiring rotary instruments that may damage gingival tissues or the tooth. However, if the wax (and therefore composite) does not extend onto the gingiva, finishing will be an easy and gentle process.

Once the desired changes have been made to the casts by removing stone and adding dental wax as described, the modified model is hereinafter referred to as the "final design model". As noted, a variety of functional and aesthetic conditions can be improved using the present invention. Examples include fractures, gaps, wear, and rotations, malpositions, and malocclusions. Care must be taken to ensure that the desired changes are performed on the tooth models in an exacting manner. The transfer technique is highly accurate, and any changes represented by the wax contours, on the plaster model, will be reproduced on the teeth in the patient's mouth.

Figure 3:
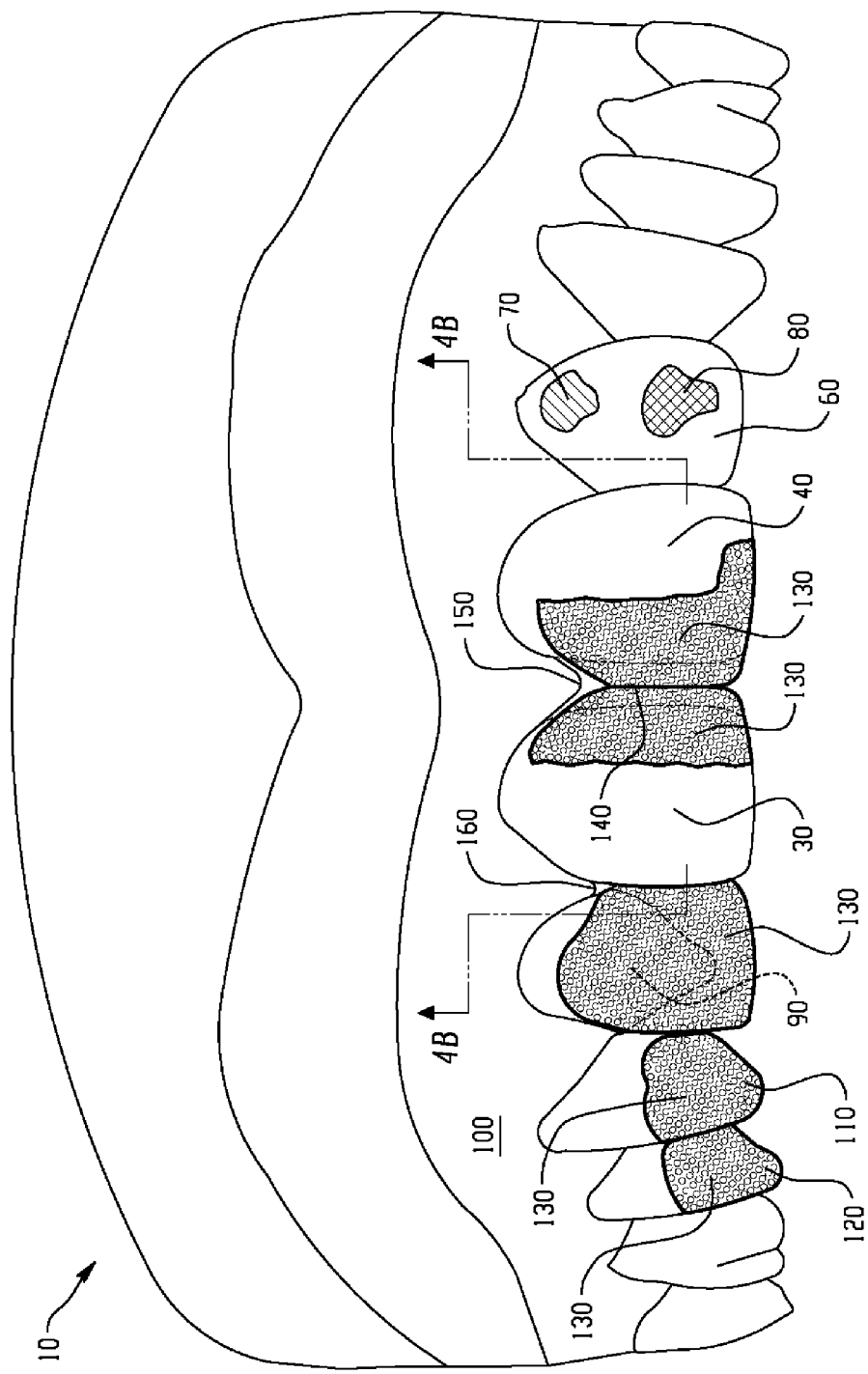
FIG. 3 shows the cast of FIG. 2 after wax has been applied over deficiencies.

FIG. 3 shows the cast 10 of FIG. 2 after wax 130 has been applied. Specifically, wax 130 has been applied to both the right central incisor 30 and the left central incisor 40 to close the diastema 20 shown in FIG. 2. The wax 130 forms an interproximal contact 140 between such teeth and extends approximately one-third of the way across the facial sides of both teeth. It will be appreciated that the amount of wax 130 to be added to the cast 10 will depend on each particular case, and that a one-third extension beyond the interproximal contact 140, while appropriate in this particular instance, is merely exemplary. Wax 130 has also been applied to the right lateral incisor 90, which is shown in phantom (dashed) lines, to form a tooth that is functional and aesthetically acceptable. Wax 130 has also been applied to the right canine/eye tooth 110 and right first premolar 120 to correct the contours thereof. It should be noted that there is a space 150 between the patient's current papilla and the interproximal contact 140 between the right central incisor 30 and the left central incisor 40. A smaller space 160 also exists between the patient's current papilla and the interproximal contact between the patient's right lateral incisor 90 and right central incisor 30. After restoration of the patient's teeth in accordance with the method of the invention, the papilla will gradually fill and close these spaces 150, 160.

Figure 4A:
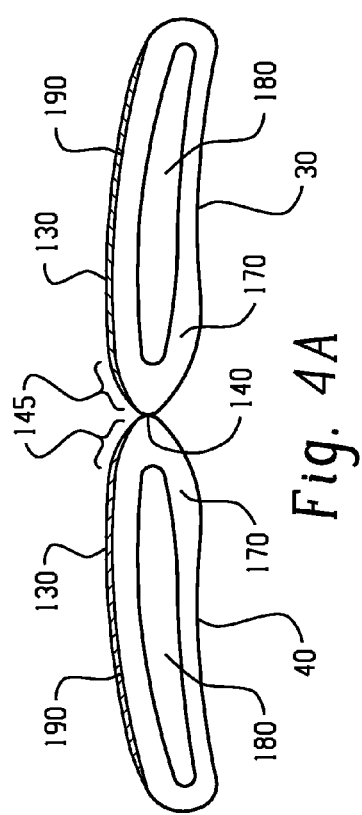
FIG. 4A is a horizontal (X-plane) section view taken through a set of adjacent teeth in the cast of FIG. 3.

FIG. 4A is a horizontal (X-plane) section view taken through two central incisors 30, 40 (not from the patient's teeth from which cast 10 has been made) that have acceptable existing interproximal contacts 140. Wax 130 has been added to the facial surface 190 and the interproximal contact zone 145 of the teeth 30, 40 for various functional or aesthetic purposes. However, wax 130 does not add dimension to the existing interproximal contact 140. The section view shows the enamel 170 and dentin 180 portions of each tooth. It should be noted that the wax 130 thins or feathers in the interproximal contaxt zone 145 before the interproximal contact 140 between such teeth.

Figure 4B:
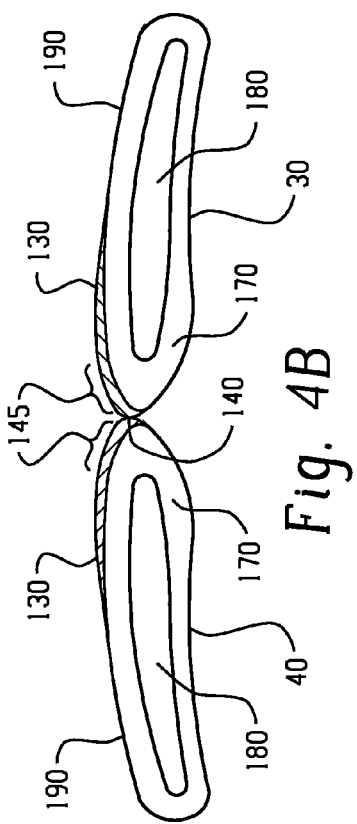
FIG. 4B is a horizontal (X-plane) section view taken through another set of adjacent teeth in the cast of FIG. 3.

FIG. 4B is a horizontal (X-plane) section view taken through the two central incisors 30, 40 from the patient's teeth from which cast 10 has been made. An interproximal contact 140 has been created using wax 130. Wax 130 extends from the interproximal contact 140 through the interproximal contact zone 145 and onto portions of the facial surface 190 of the teeth 30, 40. The diastema 20 shown in FIG. 1 has thus been closed. The interproximal contact 140 between such teeth is very small, and can be easily opened and separated as further described below. The section view also shows the enamel 170 and dentin 180 portions of each tooth. The dimensions and contours of the incisors 30, 40 shown in FIG. 4B will be identical to the dimensions and contours of the incisors 30, 40 shown in FIG. 4A after restoration has been completed.

It will be appreciated that the final design model need not be made of a single, unitary piece of dental stone to which wax has been applied. It would be possible, for example, to form a composite final design model that included "dies" or sections of individual teeth or several teeth. It may be possible for the dies or sections to be separately waxed up or prepared as separate component parts and re-joined or reseated to the arch.

After the final design model is completed, a stent is made. The stent is used to carry the flowable and curable composite polymer tooth restoration composition to the patient's teeth to be restored and duplicate the contour and dimension of the final design model. There are three preferred methods for forming the stent. It is important that the stent:

1. record the final design model contour and dimension with the greatest accuracy and detail possible;
2. has a combined rigidity and flexibility that allows it to carry the flowable and curable composite polymer tooth restoration composition to the mouth, be fully seated into all undercuts, yet maintain original detail without distortion;
3. be small enough for easy and relatively comfortable insertion into the patient's mouth; and
4. allow curing of the restorative material through the mold, preferably using light.

It is also preferably that the stent be sized and designed such that it functions as an isolation device (i.e., it encourages the patient's lips and tongue not to interfere during treatment).

These goals are effectively accomplished with:

1. adaptation and curing of the stent under positive and/or negative atmospheric pressure. This assures the absolute highest possible degree of accuracy and detailed duplication of the original final design model; and
2. a stent that includes both a rigid or semi-rigid "skeleton" and flexible and transparent "core" or inner layer that covers portions of teeth to receive additive restoration. This combination allows the mold to carry the flowable and curable composite polymer tooth restoration composition with proper viscosity to the mouth, be inserted and fully seated without distortion.

Figure 6:
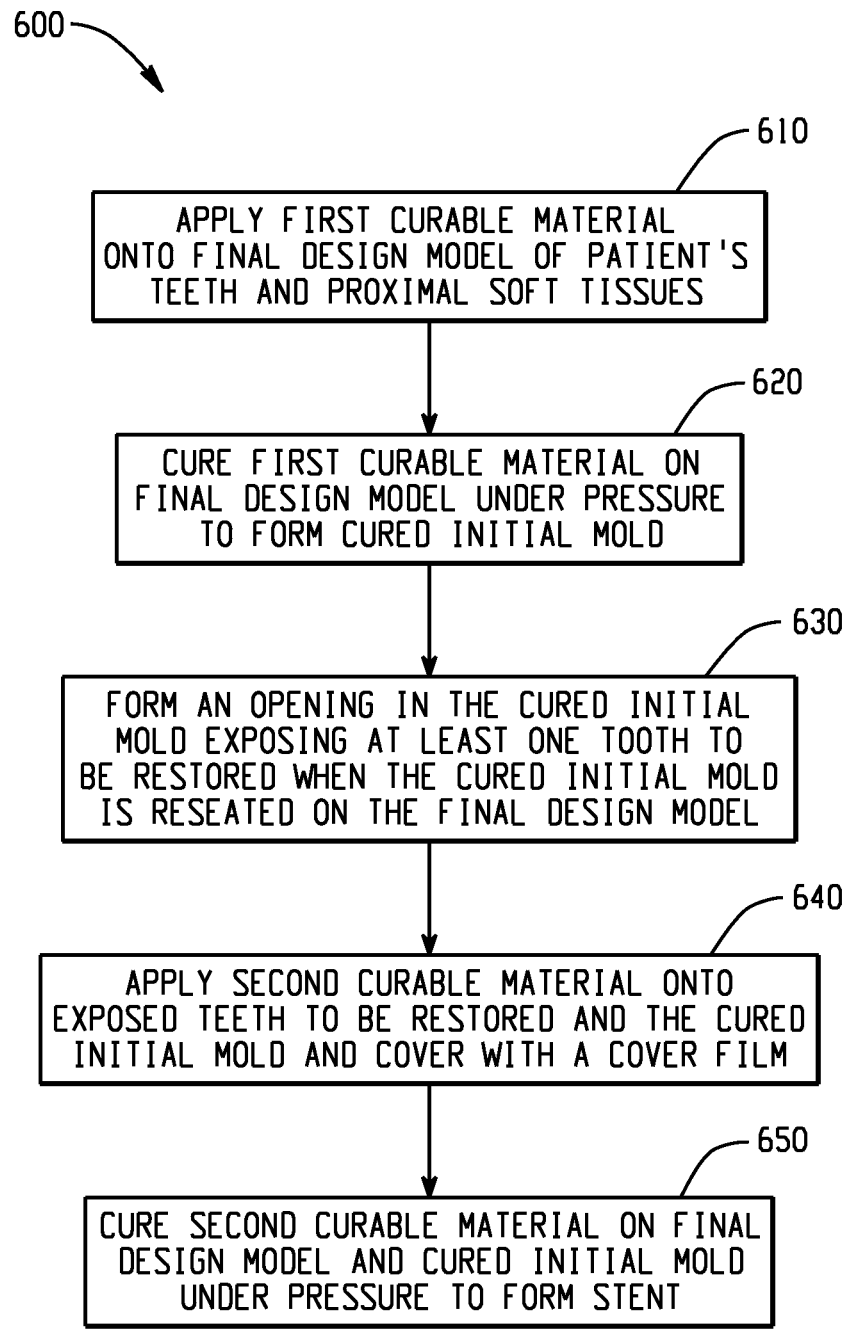
FIG. 6 is a flow chart showing the steps of a method of forming a stent according to a first embodiment of the invention.

FIG. 6 is a flow-chart that explains the steps of forming a stent according to a first embodiment 600 (hereinafter sometimes referred to as "Stent Design 1") of the invention. In a first step 610, a semi-rigid (e.g., Shore Hardness 80) putty silicone material is adapted over the final design model including teeth to be restored, adjacent teeth not being restored, and as much proximal soft tissue facial and lingual of the teeth as necessary to retain the flowable and curable composite polymer tooth restoration composition in the desired location. It should be noted that no rubber dams are used and that a seal is intentionally formed between the patient's soft tissues and the stent to help retain the flowable and curable composite polymer tooth restoration composition in the desired location and to minimize flash that must be removed after curing. This first layer of curable material should be approximately 5-10 mm thick to assure adequate rigidity, and the borders should be rounded to assure patient comfort.

After manual adaptation of the putty-silicone in the first step 610, and prior to its curing, in a second step 620 the final design model and initial mold are placed in a pressure chamber, where it cures under pressure. The amount of pressure should be sufficient to conform the putty-silicone material to the final design mold but not so great as to distort or damage the final design mold. A pressure of between about 20 psi to about 100 psi, and most preferably from about 60 to about 80 psi, is suitable. After curing is complete, the initial mold is gently removed from the final design model. This can be done with one hand holding the final design model while the fingers of the other hand gently removing the mold.

In a third step 630, an opening (hereinafter sometimes referred to as a "window") is cut through the initial mold removing only those portions of the initial mold that cover portions of the final design model where composite is to be added. This is effectively done with a laboratory scalpel or razor knife. Typically, cutting is performed on the initial mold while it is separated from the final design model. An amount of material should be retained sufficient to create a "positive stop", which will insure accurate re-seating of the final stent in the patient's mouth without distortion. The opening or window should extend to an area just below the soft tissue area. After the window has been formed, the initial mold is reseated on the final design model.

In a fourth step 640, second curable composition is then disposed into the window(s) replacing the putty silicone that was cut away. The second curable composition must be able to very accurate register the contours of the final design model. Preferably, it is sufficiently transparent to light to facilitate the curing of flowable and light-curable composite polymer tooth restoration compositions disposed in the impression formed after curing the second material. A clear flexible silicone bite registration materials having a Shore hardness that is less than the putty-silicone (e.g., 72) are suitable for this purpose. This material can be applied to the interface between the initial mold and the final design model of the patient's teeth using a syringe or other dispensing device. It is advisable to use puffs of compressed air to force the material into crevices, depressions, holes and undercuts in order to ensure that extremely accurate contours are obtained after curing. The material can be applied in small amounts to such areas and then be blown in using air before the remainder of the material is added. It is advantageous to cool the silicone material prior to use to extend its working time before cure. The second curable composition (e.g., silicone) can be effectively applied in adjacent rows until the entire window removed from the cured first initial mold has been filled. A cover film that is sufficiently transparent to light to light to facilitate the curing of flowable and light-curable composite polymer tooth restoration compositions disposed in the impression formed after curing the second material can be placed over the uncured second composition. Use of a cover film ensures even distribution of the second curable composition in the following step, and also provides a comfortable smooth surface when the stent is placed into the patient's mouth.

In a fifth step 650, the initial mold and final design model are then put back in the pressure vessel under pressure to cure the transparent flexible silicone material. The amount of pressure should be sufficient to conform the second curable material in the window to the final design mold, but not so great as to distort or damage the final design mold or to cause the second curable material to be forced between the initial mold and the final design mold, which would result in inaccurate seating of the stent on the patient's teeth. It will be appreciated that the amount of pressure required will be related to the viscosity of the material. Thus, a range of pressures (e.g., from about 20 psi to about 100 psi) can be used. A pressure of about 80 psi is suitable for some highly filled composite materials. One should avoid taking any action that will create bubbles in the second curable material during curing, or will cause lifting of the cover film during curing. However, some bubbles and voids can be present in the stent provided the integrity of the stent necessary to obtain proper registration on the teeth is maintained and the contours of the teeth impressions are not adversely affected.

The resulting stent, which comprises a combination of cured first material (e.g., semi-rigid putty silicone), a cured second material (e.g., flexible clear silicone) and a cover film, is removed from the final design model in the same way the putty silicone mold was previously removed from the final design model. This is the most commonly used of the final mold designs, especially when only anterior teeth are being restored.

Figure 10:
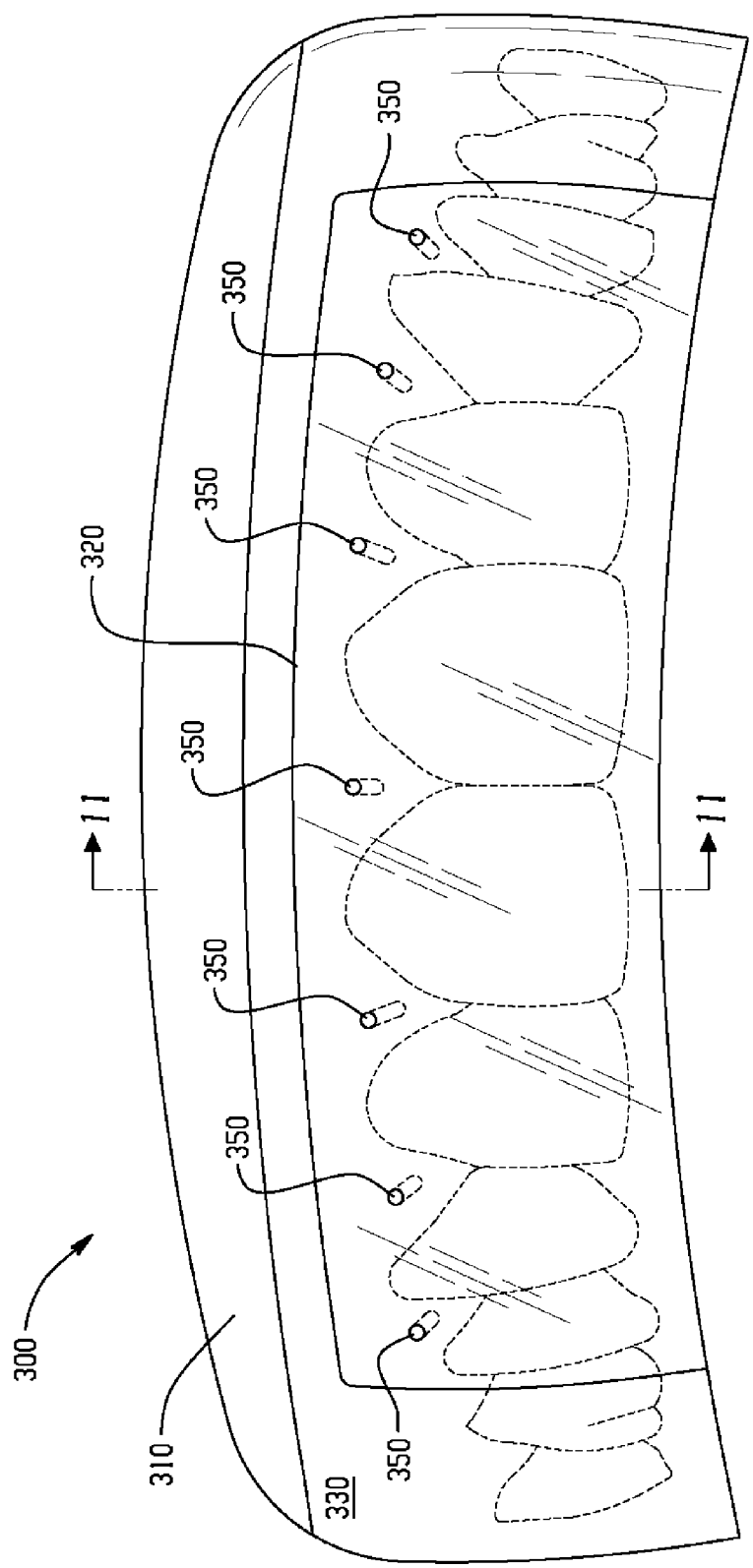
FIG. 10 is a front view of a stent according to the first embodiment of the invention.
Figure 11:
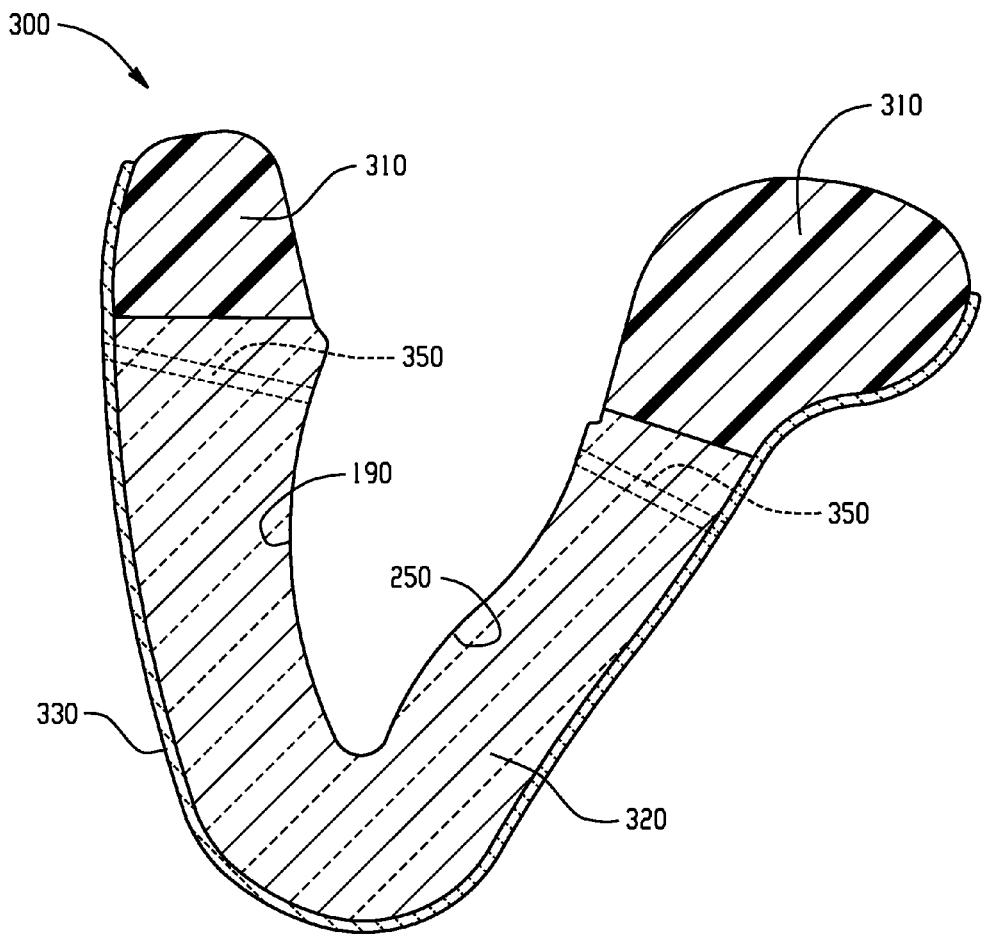
FIG. 11 is a vertical slice (Y-plane) taken through the stent shown in FIG. 10.

FIG. 10 is a front view of a stent 300 according to Stent Design 1. FIG. 11 is a vertical slice (Y-plane) taken through the stent 300 shown in FIG. 10. The stent 300 includes portions formed of the cured first material 310, the cured second material 320 and the cover film 330 (which may be removed, if desired). The stent 300 is in the form of a tray, which can be positively seated on the patient's existing teeth and soft tissues after an appropriate amount of uncured dental composite material has been placed into the tray.

Figure 7:
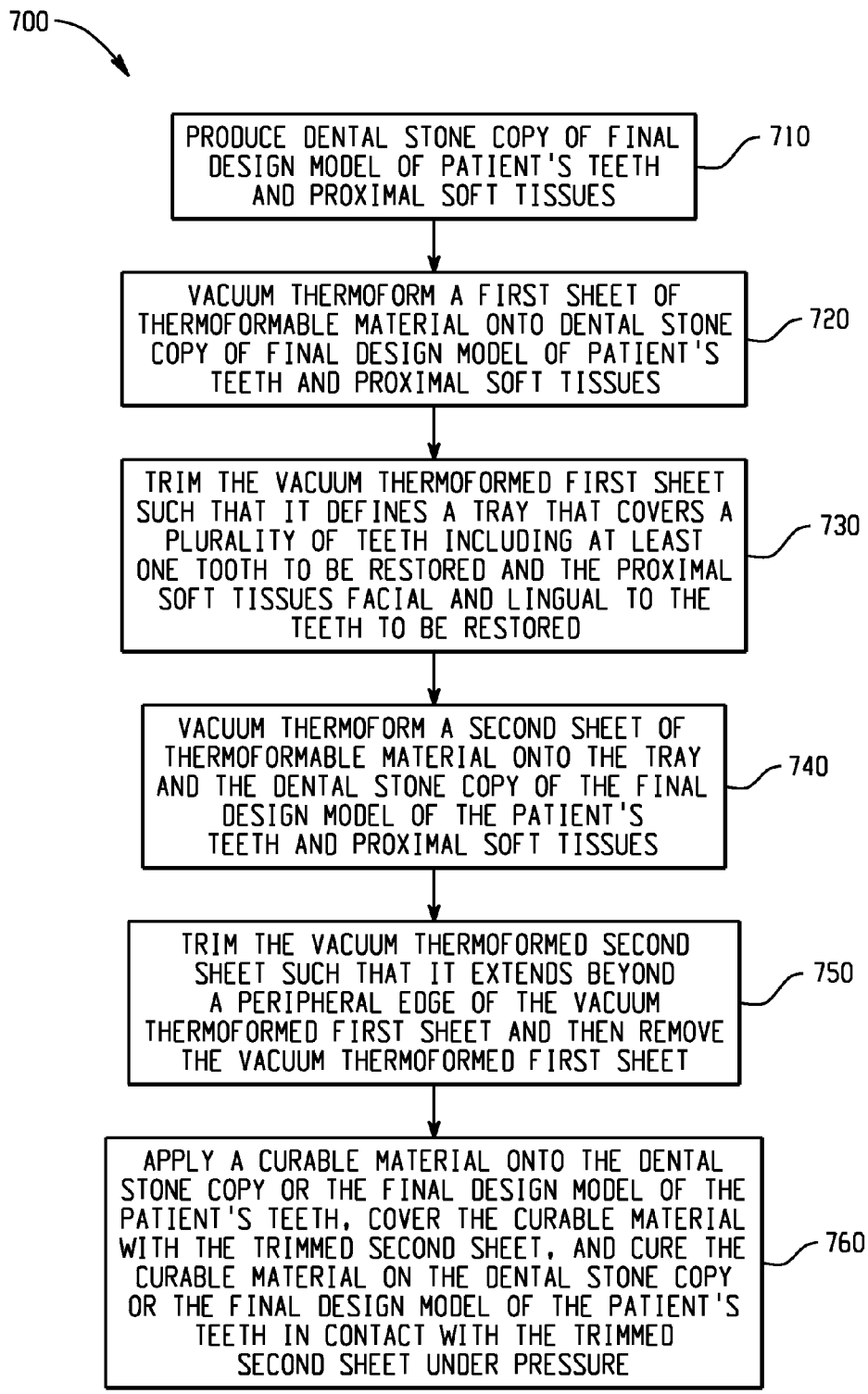
FIG. 7 is a flow chart showing the steps of a method of forming a stent according to a second embodiment of the invention.

FIG. 7 is a flow-chart that explains the steps of forming a stent according to a second embodiment 700 (hereinafter sometimes referred to as "Stent Design 2") of the invention. The second embodiment is most useful when adding to full arches or in patients with small mouth openings, because the final stent dimensions are smaller. In a first step 710, a duplicate of the original final design model is made by making an impression of the original final design model and pouring the impression with dental stone. Thus, unlike the original final design model, which is a combination of stone and wax, the duplicate final design model is made only of dental stone.

In a second step 720, a "uniform spacer" is made with a flexible thermoplastic material using a thermal vacuum/positive pressure machine. The thickness of the thermoplastic material used to fabricate the spacer is typically 2 mm, but this dimension is not critical.

Once the thermoforming is complete, in a third step 730 the thermoformed sheet is removed from the duplicate final design model and is trimmed, e.g., using scissors, such that it covers the teeth (to be restored and teeth not to be restored) and approximately 2-3 mm of soft tissues facial and lingual to the teeth. This portion constitutes the uniform spacer, which is re-adapted over the duplicate final design model and then placed back into the thermoforming equipment.

In a fourth step 740, a substantially rigid (e.g., Shore B hardness 93), transparent thermoformable thermoplastic material is then vacuum/positive pressure formed over the uniform spacer and dental stone copy of the final design model using the thermoforming equipment.

In a fifth step 750, the hard thermoformed second sheet material is then separated from the dental stone copy by cutting, e.g. using a low speed dental handpiece and cutting discs. The cut is made approximately 2-3 mm beyond the borders of the underlying uniform spacer. This portion of the rigid clear thermoplastic material (referred to as the rigid shell) and the uniform spacer are now removed from the dental stone copy of the final design model. The uniform spacer is separated from the rigid shell and discarded. The rigid shell will now fit the original final design model leaving a uniform space of approximately 1.5-over 2 mm between itself and the teeth, and 2-3 mm of soft tissue facial and lingual to the teeth, on the original final design model. It also contains a portion that will serve as a "positive stop" against the final design model during the following steps.

In a sixth step, a clear flexible silicone bite registration material (e.g., as used in Mold Design 1) is placed into the portion of the shell previously occupied by the uniform spacer in much the same manner as previously explained with respect to Mold Design 1. The rigid shell and clear bite registration material are then manually adapted over the original final design model, placed in the pressure vessel, and cured under pressure (e.g., at 80 psi). After curing, the combined rigid shell and flexible bite registration material are removed from the original final design model in the same way as the Mold Design 1 final mold was removed. Combined, the rigid shell and flexible material constitute the Stent Design 2 final mold. It should be noted that the uniform spacer represents a reasonably accurate and detailed negative duplication of the final design model and could be used in combination with the rigid shell to serve as the Stent Design 2 final mold. However, the combination of the rigid shell with the clear bite registration material cured in a pressure chamber over the original final design model is much more accurate and more detailed, resulting in a superior duplication of the original final design model.

Figure 12:
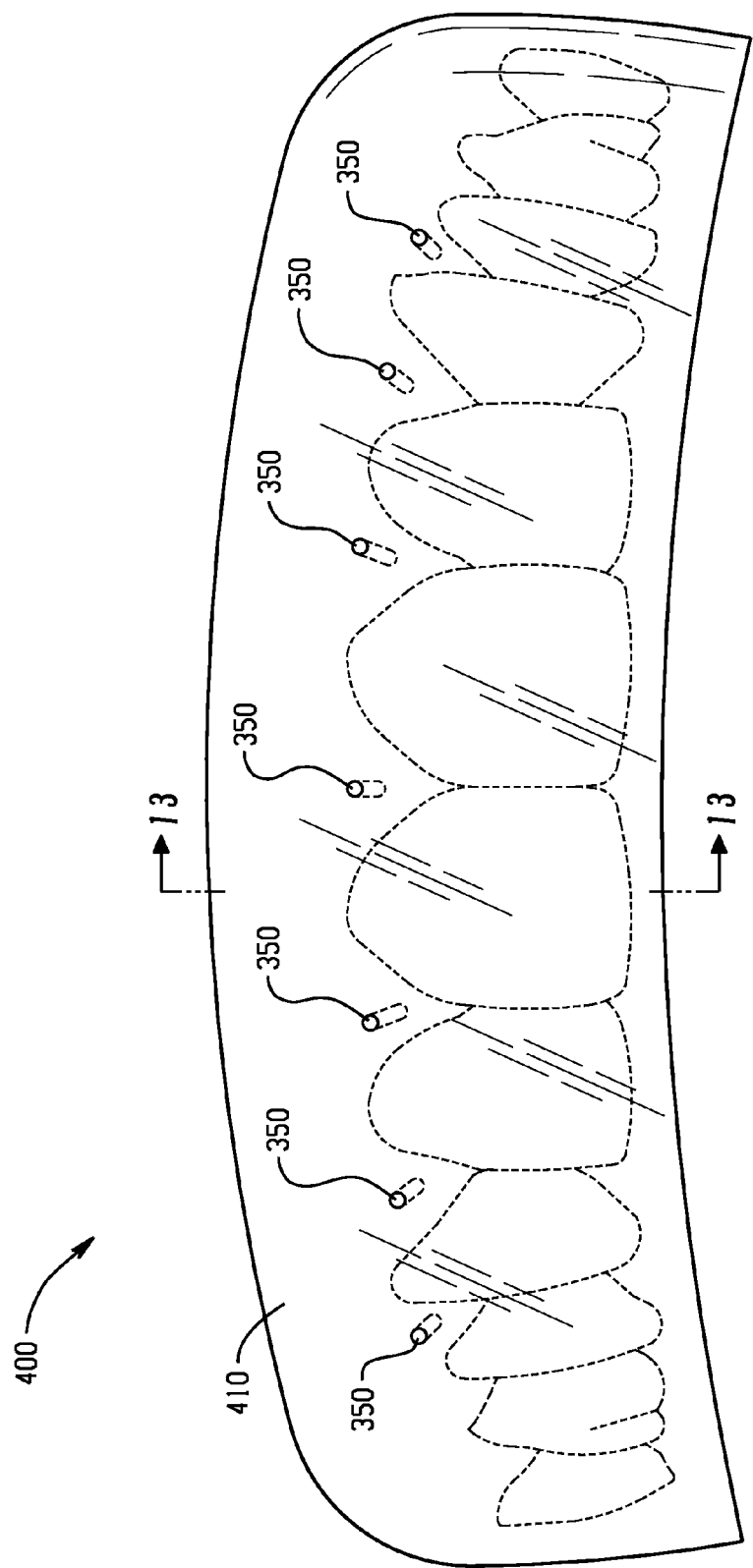
FIG. 12 is a front view of a stent according to the second embodiment of the invention.
Figure 13:
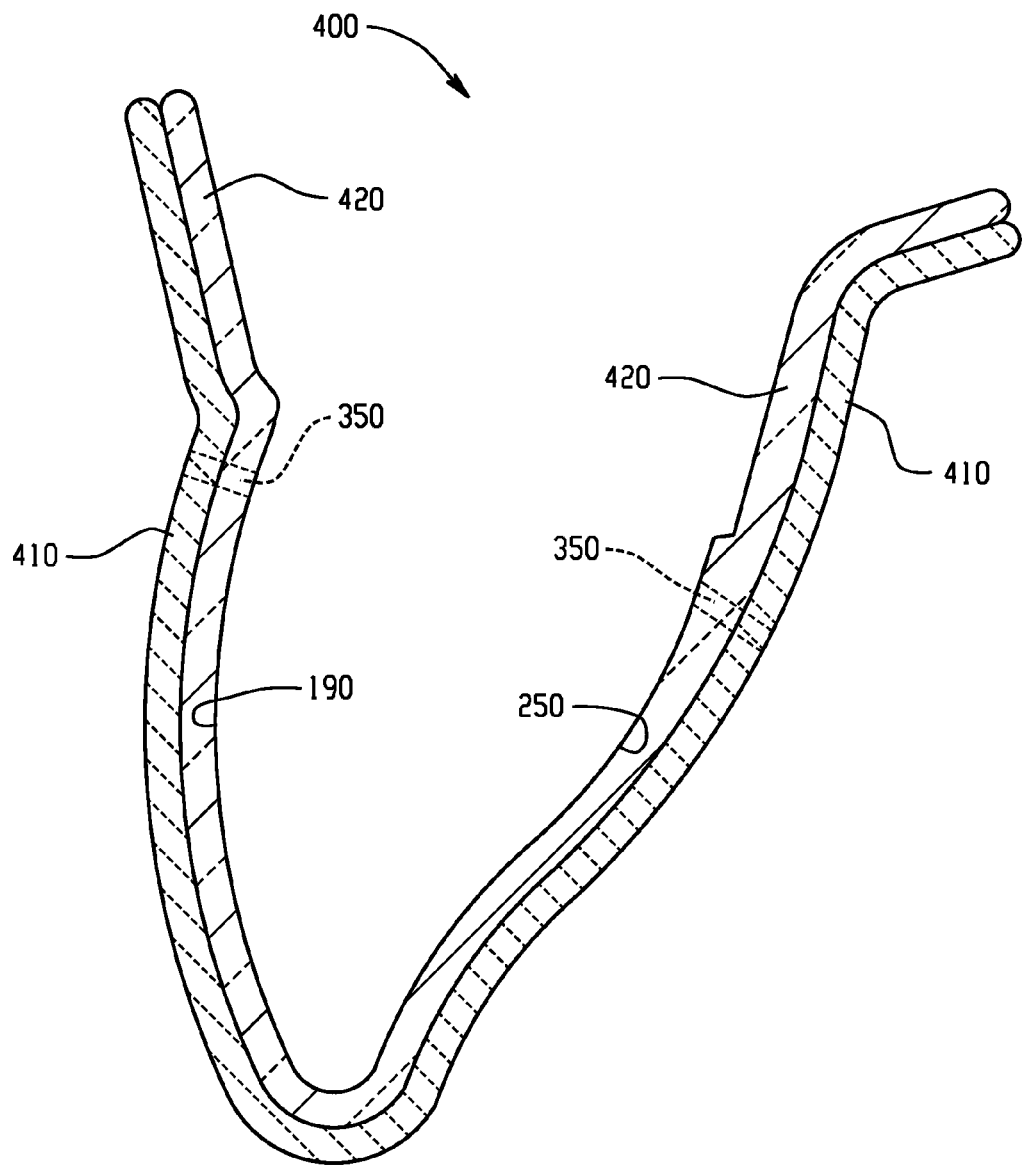
FIG. 13 is a vertical slice (Y-plane) taken through the stent shown in FIG. 12.

FIG. 12 is a front view of a stent 400 according to Stent Design 2. FIG. 13 is a vertical slice (Y-plane) taken through the stent 400 shown in FIG. 12. The stent 400 includes portions formed from the thermoformed rigid shell 410 and the cured flexible bite registration material 420. The stent 400 is in the form of a tray, which can be positively seated on the patient's existing teeth and soft tissues after an appropriate amount of uncured dental composite material has been placed into the tray.

Figure 8:
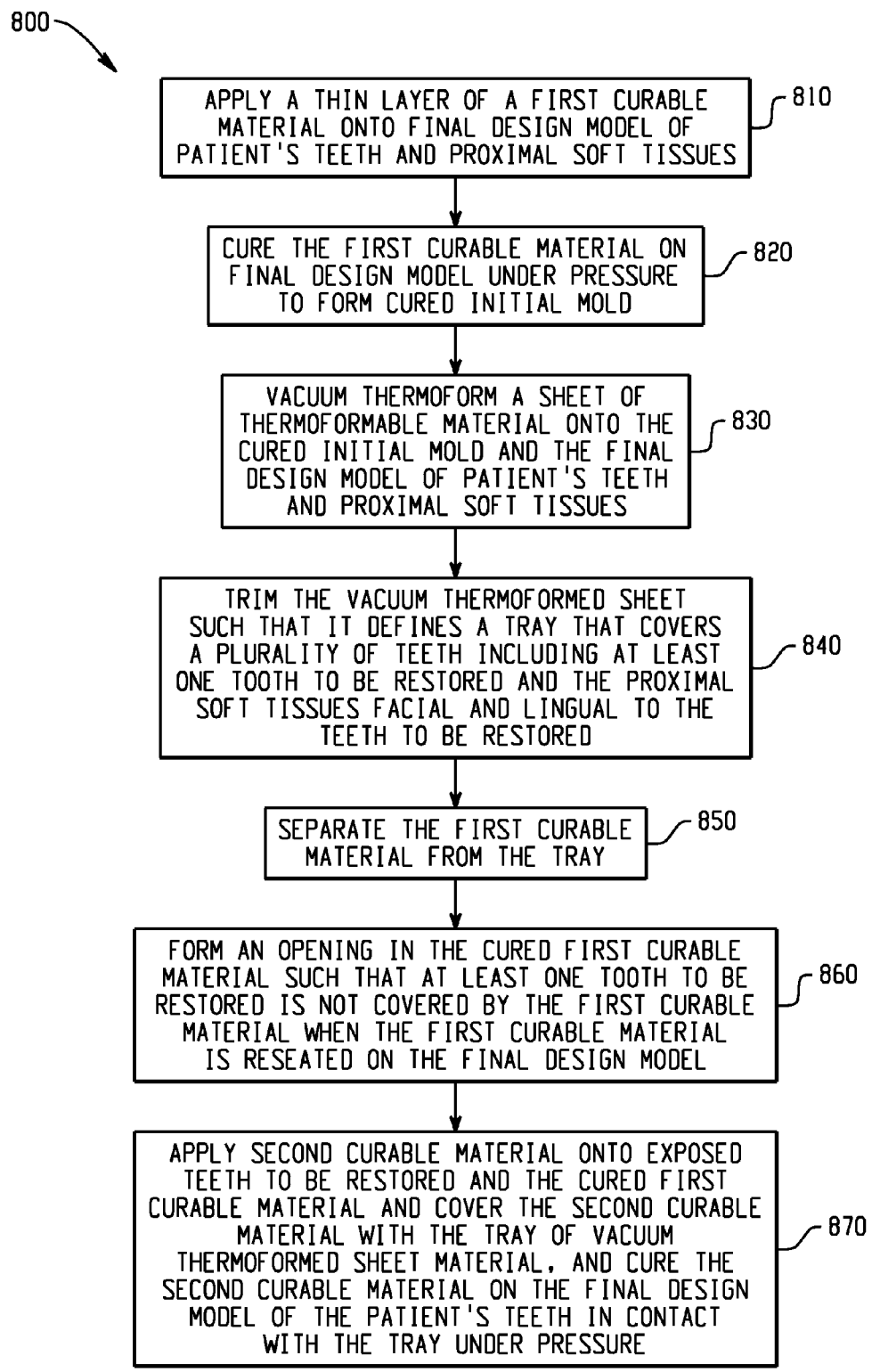
FIG. 8 is a flow chart showing the steps of a method of forming a stent according to a third embodiment of the invention.

FIG. 8 is a flow-chart that explains the steps of forming a stent according to a third embodiment 800 (hereinafter sometimes referred to as "Stent Design 3") of the invention. Stent Design 3 is similar, in some respects, to Stent Designs 1 and 2, except that in Stent Design 3, it is not necessary to produce a dental stone copy of the final design model (the stent can be formed on the wax-up) because the uniform spacer is made of putty silicone rather than a thermoformable thermoplastic sheet material. In a first step 810, a "uniform spacer" is made by adapting ~1-4 mm (preferably about 1.5 to 2.5 mm) of a first curable material (e.g., semi-rigid putty silicone_over the final design model covering all the teeth and ~2-3 mm soft tissue facial and lingual to the teeth.

In a second step 820, the first curable material is cured under pressure (e.g., 80 psi) on the final design model to form a cured initial mold.

In a third step 830, a vacuum/positive pressure machine is used to adapt a rigid clear thermoplastic material over the cured uniform spacer (initial mold) while it is seated on the final design model.

In a fourth step 840, the thermoformed material is trimmed as described in the method of forming Stent Design 2 to obtain a rigid shell. It is important to trim the thermoplastic material around the periphery at the point where the uniform spacer meets the original final design model. This assures that the rigid shell will have a stop when adapted over the final design model with the clear silicone bite registration material in following steps.

In a fifth step 850, the first curable material (uniform spacer) is separated from the rigid shell.

In a sixth step 860, an opening ("window") is formed in the first curable material such that at least one tooth to be restored is not covered by the first curable material when the first curable material is reseated on the final design model as in the method of forming Stent Design 1. It will be appreciated that the size of the window will vary from stent to stent.

In a seventh step 870, the first curable material is reseated onto the final design model and a second curable material (flexible) is applied onto the exposed teeth of the final design model to be restored through the window as described in the method of forming Stent Design 1. Again, it may be necessary to use compressed air or other means to force the second curable material into openings and crevices etc. in the final design model of the teeth in order to ensure accurate reproduction of the contours. The cured first curable material and uncured second curable material are then covered with the tray of thermoformed sheet material, and the second curable material is cured on the final design model of the patient's teeth in contact with the tray under pressure. The stent is removed form the final design model of the patient's teeth. It can be used as is, or optionally the first cured material can be further trimmed to reduce the bulk of the stent provided the stent includes sufficient rigid material to create a "positive stop" when seated in the patient's mouth.

Figure 14:
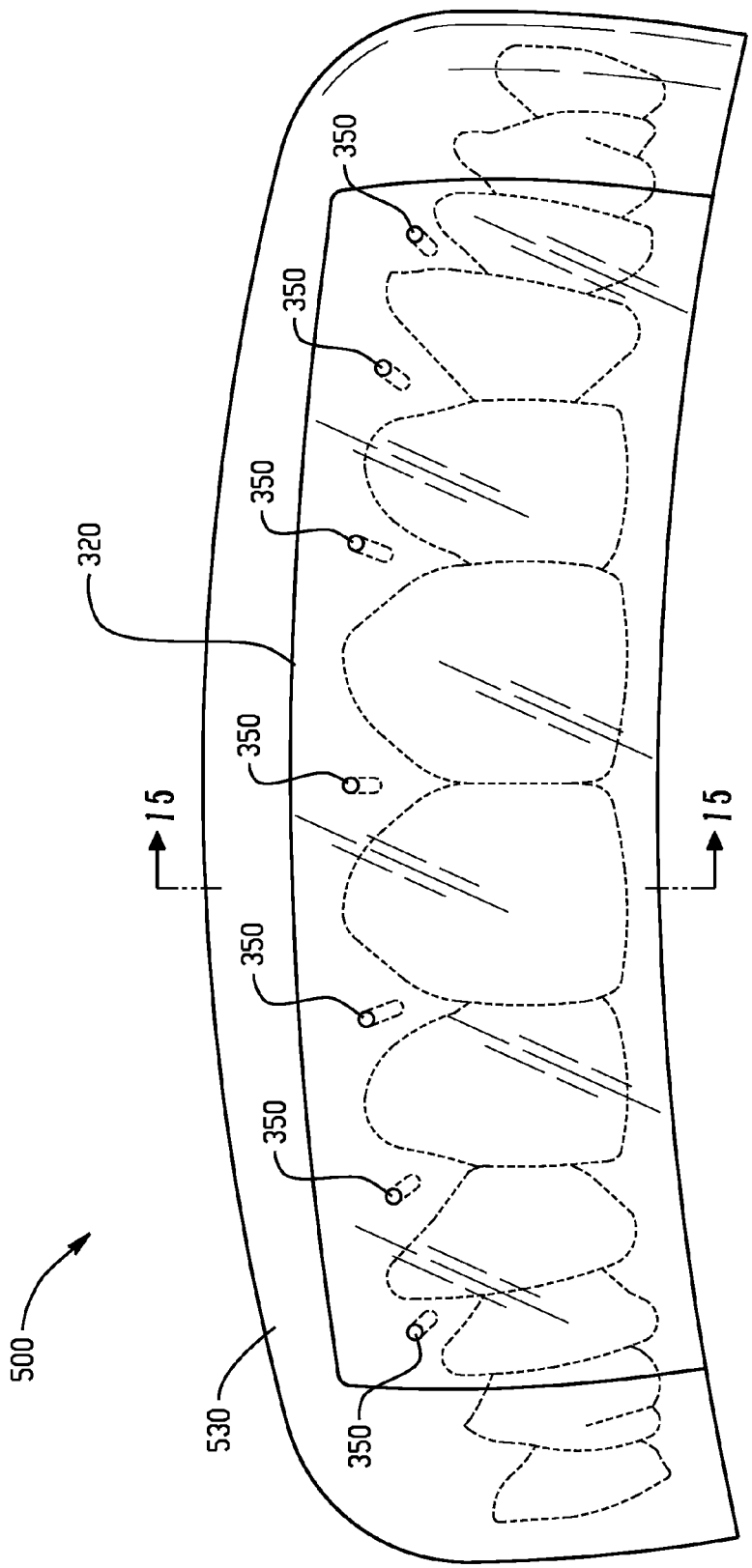
FIG. 14 is a front view of a stent according to the third embodiment of the invention.
Figure 15:
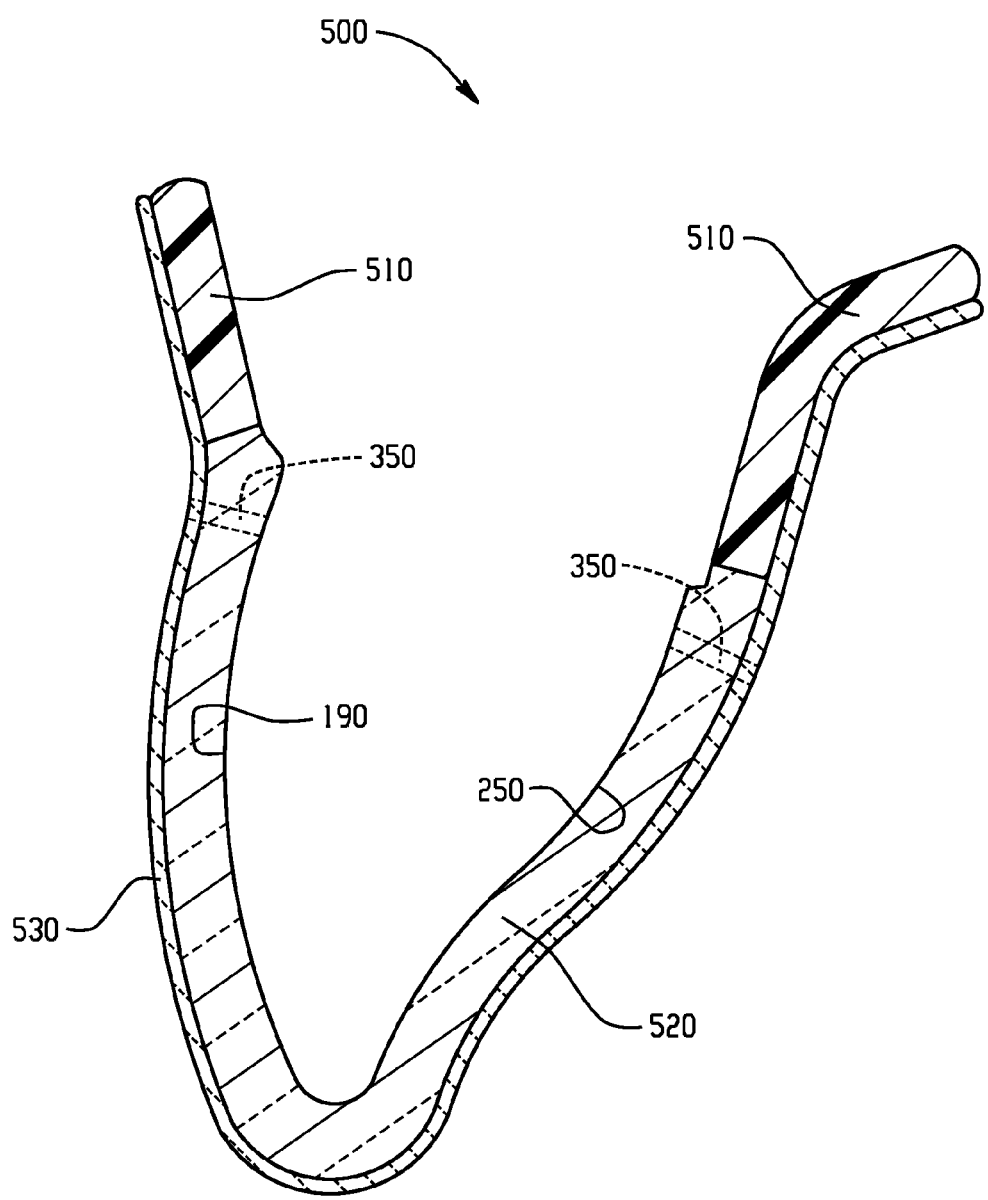
FIG. 15 is a vertical slice (Y-plane) taken through the stent shown in FIG. 14.

FIG. 14 is a front view of a stent 500 according to Stent Design 3. FIG. 15 is a vertical slice (Y-plane) taken through the stent 500 shown in FIG. 14. The stent 500 includes portions formed from the cured first curable material 510, cured second curable material 520 and thermoformed sheet material 530. The stent 500 is in the form of a tray, which can be positively seated on the patient's existing teeth and soft tissues after an appropriate amount of uncured dental composite material has been placed into the tray.

When an excess of dental composite material is placed into the stents 300, 400, 500, it may be difficult to properly seat the stents on the patient's teeth. To avoid having composite dental material flowing in spaces where it is not desired to flow, to prevent deformation of the stents and to improve the seating of the stents on the patient's teeth, it is possible to include one or more sprue holes 350 (in all designs) that allow excess composite dental material to exit from the stent when the stent is seated on the patient's teeth. The sprue holes 350 are preferably provided such that they pass through the stent opposite the papilla, both on the facial side 190 and lingual side 250 of the teeth. The patient's soft tissues can deform slightly to allow the escape of excess dental composite through the sprues, yet bias back and form a seal once the stent is perfectly seated on the teeth. The desired contours are thus maintained. After curing of the composite material, any excess dental composite remaining on the papilla can be removed by wiping or by lifting with a scalpel or IPC instrument. It does not tenaciously adhere to the papilla. In some cases, it helps with the removal of "flash", which tends to bond to the cured material formally contained within the sprue holes.

The combination of techniques and physical qualities of stents according to the invention allow the most accurate, detailed, easiest, and most time efficient application of restorative material to teeth. The techniques of mold fabrication, wax-up design and physical qualities are a key difference between the present application and the prior art. For example, in the method according Vuillemot, the mold is made of a singular clear flexible polyvinyl siloxane material. Furthermore, the material is manually adapted over the final design model without benefit of a pressure vessel. Furthermore, the mold is then drilled for injection and venting of the composite. Furthermore, this mold design requires preparation of tooth structure and addition of restorative material beyond the dimension of desired addition. These differences result in reduced accuracy, less detail, increased procedural effort and increased time requirements for restorative addition. The stents, which are patient specific, can now be used to restore the patient's teeth.

Anti-anxiety agents and anesthetics are rarely needed, but may be used if necessary. Prior to the performance of patient treatment procedures, the flowable and curable composite polymer tooth restoration composition and the final molds are preferably heated to a temperature above ambient (e.g., about 60° C.). Heating to this temperature improves the viscosity and the polymerization percentage of the restorative material.

Any necessary tooth reduction is performed on the patient's teeth as previously described above. Tooth reduction typically does not involve conventional indirect tooth restoration preparation (e.g. crown, inlay/onlay, or veneer preparations). Rather, it is limited to removal of tooth structure that:
1. is outside of planned definitive restoration contour and dimension;
2. is carious;
3. will compromise restoration structural quality (e.g. poorly mineralized dentin or enamel, or sharp external line angles); or
4. will compromise restoration aesthetic quality (e.g. discolored tooth structure or "feathering of abrupt line angles).
5. must be removed in teeth opposing restored teeth to accommodate re additions made to the restored teeth (i.e. accommodating excessive tooth structure)

This limited removal of tooth structure represents another key advantage of the current invention, as it results in restorations being created with an absolute minimum removal of tooth structure (compared to other dental techniques). Structurally acceptable, aesthetically acceptable and functionally acceptable tooth structure need not be removed in accordance with the process of the invention.

The patient should rinse with an alcohol based mouth rinse to remove contaminants from soft tissues that might interfere with bonding. Unless isolation is not possible, the following procedures of cleaning, etching, priming, bonding, and restoring are performed on all teeth to be restored in a given arch at the same time. Areas of teeth to receive restoration are preferably cleaned with either a slurry of pumice and water with a prophy cup, or with a micro-abrasion instrument with 50 micron $AlO_2$. Enamel areas to be restored are then preferably etched, with a twenty second application of 35% phosphoric acid gel, then rinsed with water. The enamel will appear a frosty white color when etched. Exposed dentin to be restored should be conditioned with a dentin priming agent. Then, both etched enamel and primed dentin are covered with a bonding agent. The bonding agent may then be light-cured either before or after insertion of the stent and restorative material over the patient's teeth. If cured prior to insertion, where adjacent teeth being restored are in contact, a metal or polyester strip can be placed between these teeth. The bonding agent is then light-cured or may be cured after the composite is applied (it will be appreciated that other etching/priming/bonding protocols may be used, provided they do not adversely affect the outcome of the process). Once the bonding agent is cured, the metal or polyester strip is removed. It should be noted that other etching, conditioning, priming, and bonding materials and protocols are acceptable—as long as they create a mechanical and/or chemical bond between the restorative material and tooth structure (or previous restorations if additions are being added over previous restorations).

After etching, priming, and bonding procedures are complete, the heated restorative material is placed into the stent in those areas where additions to the existing tooth structure are being made. A slight excess of restorative material is utilized. The amount to be added can readily be estimated by the practitioner by inspecting the final design model, and because the mold fits so tightly, excess material is easy to remove at the end of the process. At 60° C., the composite restorative material is highly flowable. The final mold (with restorative material) is inserted and completely seated on the patient's teeth. Complete seating of the final mold is easily confirmed when there is no movement or distortion of the final mold with firm hand pressure against the mold.

The restorative material is then cured. In cases where the restorative composition is light-curable, a dental curing light of at least 800 mW/cm² intensity and a usable output in the 430-480 nm range can be used. The final mold is then easily removed from the mouth with a light tugging effort. Final finishing is then done to refine both aesthetic and functional qualities of the restorations. With accurate casts, properly contoured wax-ups, properly fabricated stents, and adherence to the procedures described, post-cure finishing should be relatively simple.

Figure 9:
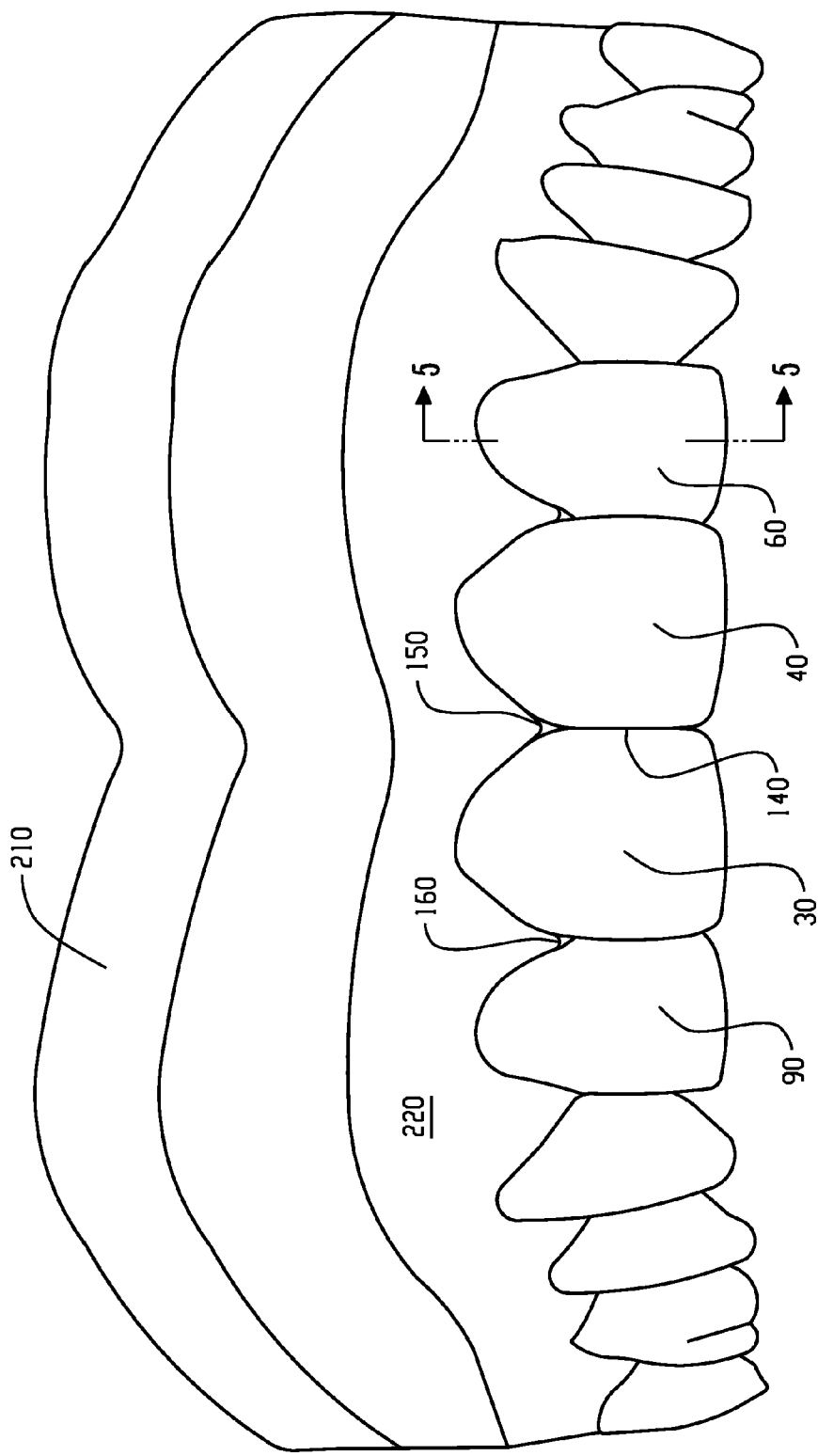
FIG. 9 is schematic front view of a patient's teeth after restoration.

FIG. 9 is schematic front view of the patient's teeth 200, which were used to form the cast 10 of FIG. 1, after the patient's teeth 200 have been restored in accordance with the invention. The patient's lips 210 have been retracted to show the patient's soft tissues 220. The teeth 200 are now symmetrical, aesthetically improved and biomechanically functional. Dental composite has been bonded to the teeth 200 as required to correct defects in contours and dimensions. As previously noted, there is a space 150 between the patient's current papilla and the interproximal contact 140 between the right central incisor 30 and the left central incisor 40. A smaller space 160 also exists between the patient's current papilla and the interproximal contact between the patient's right lateral incisor 90 and right central incisor 30. The papilla will gradually fill and close these spaces 150, 160.

Figure 5:
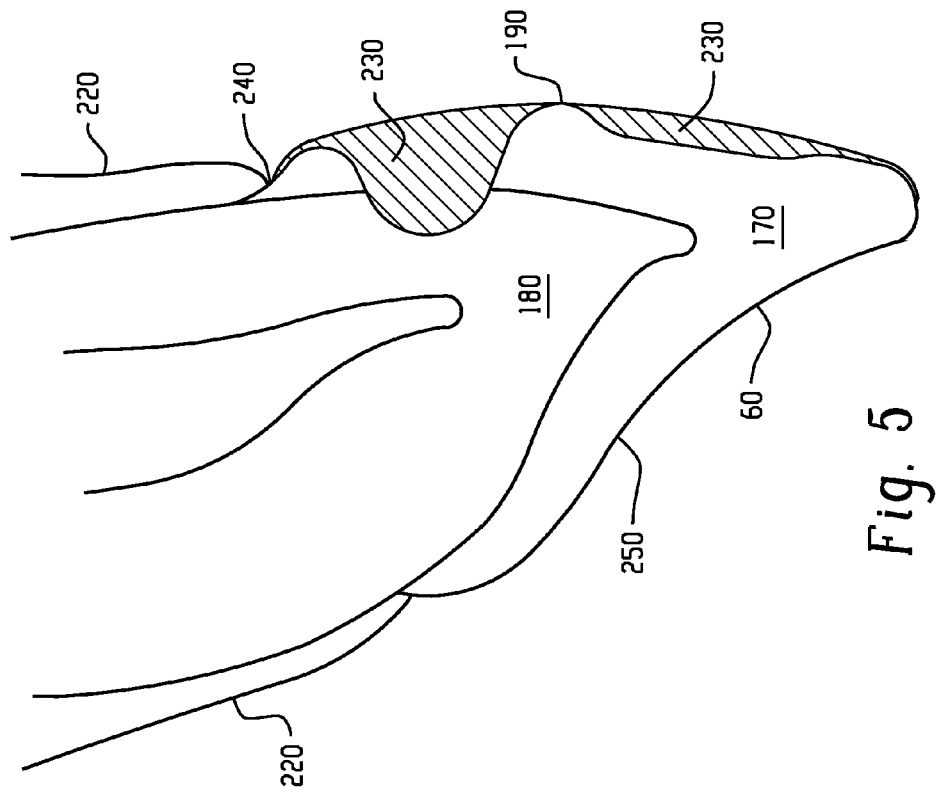
FIG. 5 is a vertical (Y-plane) section view taken through a patient's tooth and a portion of the patient's soft tissues after restoration of the tooth.

FIG. 5 is a vertical (Y-plane) section view taken through the patient's left lateral incisor 60 and proximal soft tissue 220. A portion of the enamel 170 and dentin 180 has been removed where carious tooth structure 70 (shown in FIGS. 1, 2 and 3) was present and enamel 170 has been removed where staining 80 was present on such tooth. The removed enamel 170 and dentin 180 has been replaced with dental composite material 230 on the facial side 190 of the tooth. It should be noted that the dental composite material 230 does not extend to the proximal soft tissue 220, but thins or "feathers" as it approaches the gingival crest 240. Although no dental composite material 230 was bonded to the lingual side 250 in the illustrated example, it will be appreciated that dental composite material 230 may need to be applied to the lingual side 250 of the tooth in some cases. Other changes could also have been made, if needed.

When the stent is removed from the mouth, resulting restorations should be an accurate duplication of the wax-up with a minimal amount of excess composite. Finishing procedures for the restorations involve first removing the excess composite, then separating and finishing the interproximal contacts and contact zones. These procedures involve the following steps and should be done, preferably in the order described:
 Remove excess composite from the soft tissues and restoration margins;
 Refine the interproximal contact zones and emergence areas;
 Separate the interproximal contacts; and
 Finish and polish the interproximal contacts and contact zones.

One should remove excess composite from the soft tissues and restoration margins. This step involves removing cured and uncured excess composite from the gingiva and teeth. To make this step easier, it is helpful to limit the area of tooth bonding and coverage of the transparent window of the stent to just slightly beyond where composite is being added. Uncured excess composite should be wiped off the gingiva and teeth with an alcohol sponge. Cured composite (sometimes referred to herein as "flash") that is not bonded to the tooth or is covering soft tissue should be lifted off with an interproximal carving instrument (IPC). Flash that is bonded to the tooth should be removed with an abrasive wheel or point that will remove the composite, but not harm the tooth (such as a brown point "brownie" finisher), or with a scalpel blade as described below.

The interproximal contact zones and emergence areas should be refined. This is the most sensitive and critical step in finishing the interproximal contact and contact zone. Once most of the unbonded flash is removed with an IPC instrument, there will likely still be a small amount remaining along restoration margins and in the interproximal emergence area. The interproximal emergence area is difficult to access with most instruments, but is nicely refined with a #12 scalpel blade. It is recommended that this blade be used with a round handle for the best control. It is also recommended that carbon steel blades be used and changed frequently.

The blade is first used to remove flash and refine restoration contour and margins in the interproximal emergence area. It is next used to refine the contact zone. Then, (although not a part of interproximal contact refinement), the blade is used to remove bonded and unbonded flash along facial and lingual tooth surfaces (where restorations extend to the gingival margin). Finally, the blade is used to "score" composite overlying the interproximal contact. This is to assure a clean, faultless separation of the interproximal contact in the next step.

The interproximal contacts should be separated. The ease or difficulty of this step depends upon the attention given to every procedure and protocol thus far described. If all are followed, this is a simple and quick procedure for both the dentist and patient (a typical six anterior restorations should take no more than one to two minutes). However, if they are not followed, this will likely be a long and unpleasant experience.

It is recommended that a short handle dental micro saw and saw blade be used and that the blade cut while pushing, not pulling. With light to moderate force, saw through the contact (although slightly more force may be needed with very tight or broad contacts). Typically one blade will separate many contacts, but change the blade when it dulls. Be careful not to damage the interdental papilla as the saw blade passes through the contact. If contacts do not readily separate, use the scalpel to further score the interproximal contact and refine the contact zone.

After separation of the interproximal contacts, the interproximal contacts and contact zones should be finished and polished. After the interproximal contacts have been refined and separated, it is important that they are not damaged with aggressive finishing techniques. Epitex strips are ultra thin strips that are perfect for the very delicate finishing that is still needed. They provide a combination of abrasiveness and polishing ability to finish the interproximal contact and contact zones to the highest aesthetic and hygienic standards. If the strips tear when entering the contacts, gently use saw blades again until the strips can be used without tearing. When completed, the interproximal contacts and margins should be as smooth and hygienic as those of healthy teeth.

It will be appreciated that the process according to the invention can be utilized to apply layers of tooth composition to a patient's teeth, if desired. For example, an opaque layer may be applied in a first step and then a more transparent layer may be applied in a second step to provide a final restoration that appears to have greater "depth" than would otherwise be achievable in one step. This method allows for the application of different colors and optical qualities.

It will be appreciated that in addition to differences between the stents used, and also the resultant methodology for adding the restorative material with each stent, the present invention provides improvements over the prior art in that prior art methods for restoring teeth in situ cannot be used to restore adjacent teeth simultaneously. Rather, prior art methods utilize an "every other tooth" protocol, requiring restorations being fabricated in two applications. In contrast, procedures used in the current invention restore adjacent teeth simultaneously. This results in a more accurate duplication of the original tooth model design. It is also easier and more time efficient. Release agents used in the "every other tooth" protocol add dimension to the teeth in the mouth that is not accounted for during mold fabrication. This results in distortion of the mold (and therefore the restorations) during seating. In addition, inaccuracies created from this distortion with the first application will be compounded when the mold release agent is once again used prior to the tray being inserted for the second application. In addition, the time needed to add restorative materials in multiple applications adds complexities and time to the procedure. The additional time and effort required for this protocol far exceed those needed to separate and refine adjacent tooth contacts when adjacent teeth are restored simultaneously—as a part of this invention's methodology.

The following example is intended only to illustrate the invention and should not be construed as imposing limitations upon the claims.

EXAMPLE

A thirty year-old male patient with minimal existing restorations and no active caries or periodontal disease presented with biomechanical and aesthetic issues. He had moderate to severe tooth wear, sensitive teeth, and was unhappy with his smile. He said he was not chewing well and wanted to improve his smile and eliminate tooth sensitivity. He was prepared to have indirect ceramic restorations placed, but wanted to remove as little tooth structure as possible in the process. He also indicated that, to do indirect ceramic restorations, he would need to phase treatment over three to five years.

The patient's biomechanical evaluation determined that he had manageably adapted TM-joints, a posterior dysfunction functional occlusion, and benign or structural parafunctional activity. Patients with this combined biomechanical status can safely proceed with definitive restorative and aesthetic treatment—as long as the Functional Occlusion is corrected as a result of treatment. Such patient's can also benefit from developing a Stable Biomechanical Foundation prior to definitive tooth preparation. Because this patient wanted to phase treatment over three to five years, he was also an excellent candidate for using the process according to the invention.

Evaluation of radiographs, photographs, and mounted casts of the patient indicated that his vertical dimension would need to be opened from that of first tooth contact with the condyles physiologically seated. As in all cases requiring vertical opening, it was opened the least amount possible to achieve an ideal functional aesthetic outcome.

A modified AACD photographic series then guided a preliminary functional aesthetic wax-up at this vertical dimension. A stent duplicating this wax-up was then filled with a chemically curable veneer composition and transferred to the patient's mouth. This allowed confirmation and modification of aesthetic and functional qualities of the wax-up.

After adjustment and confirmation of the design, a final full contour wax-up was made. In this case, no existing tooth structure was outside the final functional aesthetic design. Therefore, Stable Biomechanical Foundation development and interim restoration fabrication would be a purely additive process.

Once the final full contour wax-up was completed, upper and lower stents were fabricated. To meet the requirements of the restoration process, the stents had to (1) record the wax-up design with the greatest accuracy and detail possible; (2) exhibit a rigidity and flexibility that allow it to carry the highly-filled, flowable and curable composite to the mouth, be fully seated into all undercuts, yet maintain original detail without distortion; (3) be small enough for easy insertion into the mouth; and (4) allow light curing of the composite through the stent.

These requirements were effectively accomplished using a putty silicone stent with a transparent silicone inlay in a window covering all teeth where composite was to be added (i.e., Stent Design 1). When fabricated properly, and cured under pressure, this stent design is extremely accurate and captures the finest of detail.

The choice of composite material was made in view of combined physical and optical properties. Ideal physical handling and performance properties of a composite for the process include (1) a viscosity that gives the best duplication of original wax-up detail, yet minimizes stent deformation during seating; (2) fracture resistance similar to natural tooth structure; (3) wear resistance and abrasiveness similar to enamel; and (4) luster similar to enamel. Ideal optical properties include: (1) light refraction, reflection, and fluorescence similar to those of natural tooth structure; (2) a high chameleon quality (a visual quality of blending in with surrounding tooth structure); and (3) availability in a range of shades and opacities to duplicate natural occurring teeth. Unfortunately, no material commercially available possesses all these qualities.

The chairside portion of the process involved eight steps:
1. Heating the stent and curable restoration composite to 60° C. to improve the polymerization and viscosity of the composite;
2. Etching the patient's enamel where material was to be added, applying primer to exposed dentin and applying and drying adhesive per the recommendations of the manufacturer;
3. Disposing the heated composite in the stent where material was to be added to the patient's teeth;
4. Inserting and fully seating the stent in the patient's mouth;
5. Light-curing the composite through the flexible silicone window;
6. Removing the stent and completing curing using light;
7. Separating interproximal contacts, finishing and polishing the restorations; and
8. Refining the occlusion.

In this case, interproximal contacts were separated and refined with dental saw blades and/or scalpels, and Epitex interproximal strips. The occlusion was refined with a high-speed bur and silicone polisher points, and the restorations polished with polishing discs.

For the twenty-eight restorations made in this case, application and finishing took three and one half hours. It is difficult to categorize whether the restorations represent "interim" or "definitive" restorations. The Glossary of Prosthodontic Terms defines an "interim restoration" as one that is intended to serve for a limited period of time and that is to be replaced by a "definitive restoration". A "definitive restoration" is defined as a restoration that is intended for long-term use. No other qualities or time specifications differentiate interim from definitive restorations. One thing that is clear is that a decision to classify these restorations as interim or definitive depends upon more than the physical and optical qualities of the restorations. It also depends upon the attitudes of the patient. Many patients (include the patient described in this Example) want the very least invasive treatment that will achieve their functional and esthetic goals. They would prefer a restoration that will require more frequent replacement knowing that it will require less tooth reduction. Since replacing restorations made with this invention with conventional indirect ceramic or metal restorations will virtually always require the removal of more tooth structure, in this situation, it does not seem improper to consider these restorations as definitive.

If the restorations were to be considered interim restorations, they would remain in place until they are replaced with definitive restorations. This may be done with simultaneous preparation of both arches, one arch at a time, by quadrant, or one tooth at a time—in a time manner and sequence that are comfortable for the dentist and patient.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A method for forming a stent for dental restoration, the method comprising:
   applying a first curable material onto a final design model of a patient's teeth and proximal soft tissues, said first curable material
      (a) covering a plurality of teeth including at least one tooth to be restored, and
      (b) contacting the proximal soft tissues facial and lingual to the at least one tooth to be restored;
   curing the first curable material on the final design model under pressure to form a cured initial mold;
   forming an opening in the cured initial mold, said opening exposing at least a portion of the at least one tooth to be restored when the cured initial mold is seated on the final design model of the patient's teeth;
   applying a second curable material onto the exposed at least one tooth to be restored and the cured initial mold when the cured initial mold is seated on the final design model of the patient's teeth;
   covering the second curable material with a cover film;
   curing the second curable material on the final design model and the cured initial mold under pressure to form the stent having a first portion formed of the first curable material and a second portion formed of the second curable material; and
   removing the stent from the final design model to expose a mold cavity that defines contours of the final design model of the patient's teeth and proximal soft tissues.

2. The method according to claim 1 wherein the first curable material has an average thickness of about 5 mm to about 10 mm after curing.

3. The method according to claim 1 wherein the first curable material is more rigid than the second curable material after both have been cured.

4. The method according to claim 1 wherein the second curable material, after curing, is sufficiently transmissive of light within the wavelength of 400 nm to 500 nm to cure a light-curable dental composition disposed in a portion of the mold cavity that defines contours of the portion of the at least one tooth to be restored.

5. The method according to claim 1 wherein the final design model of the patient's teeth and proximal soft tissues is formed by adding wax to a cast model of the patient's teeth and proximal soft tissues.

6. The method according to claim 1 wherein the final design model of the patient's teeth and proximal soft tissues is formed by removing material from a cast model of the patient's teeth and proximal soft tissues and adding wax to the cast model of the patient's teeth and proximal soft tissues.

7. A method for forming a stent for dental restoration, the method comprising:
   thermoforming a first sheet of thermoformable material onto a final design model of a patient's teeth and proximal soft tissues;
   trimming the thermoformed first sheet such that it defines a tray, said tray covering
      (a) a plurality of teeth including at least one tooth to be restored, and
      (b) the proximal soft tissues facial and lingual to the at least one tooth to be restored;
   thermoforming a second sheet of thermoformable material onto the tray and the final design model of the patient's teeth and proximal soft tissues;
   trimming the thermoformed second sheet such that it extends beyond a peripheral edge of the thermoformed first sheet;
   separating the thermoformed second sheet from the thermoformed first sheet;
   applying a curable material onto the final design model of the patient's teeth or the final design model of the patient's teeth and proximal soft tissues;
   covering the curable material with the thermoformed second sheet;
   curing the covered curable material on the final design model under pressure to form the stent having a first portion formed of the curable material and a second portion formed of the thermoformed second sheet; and
   removing the stent from the final design model to expose a mold cavity that defines contours of the final design model of the patient's teeth and proximal soft tissues.

8. The method according to claim 7 wherein the first sheet of thermoformable material has a thickness of about 0.5 to 4 mm.

9. The method according to claim 7 wherein the thermoformed second sheet is more rigid than the curable material after it has been cured.

10. The method according to claim 7 wherein both the thermoformed second sheet and the curable material, after curing, are sufficiently transmissive of light within the wavelength of 400 nm to 500 nm to cure a light-curable dental composition disposed in a portion of the mold cavity that defines contours of the at least one tooth to be restored.

11. The method according to claim 7 wherein the final design model of the patient's teeth and proximal soft tissues is formed by making an impression of a cast model of the patient's teeth and proximal soft tissues to which wax has been added, and pouring the impression with dental stone.

12. The method according to claim 7 wherein the final design model of the patient's teeth and proximal soft tissues is formed by making an impression of a cast model of the patient's teeth and proximal soft tissues from which material has been removed and to which wax has been added, and pouring the impression with dental stone.

13. A method for forming a stent for dental restoration, the method comprising:
   applying a first curable material onto a final design model of the patient's teeth and proximal soft tissues, said first curable material
      (a) covering a plurality of teeth including at least one tooth to be restored, and
      (b) contacting the proximal soft tissues facial and lingual to the at least one tooth to be restored;
   curing the first curable material on the final design model under pressure to form a cured initial mold;
   thermoforming a sheet of thermoformable material onto the cured initial mold;
   trimming the thermoformed sheet such that it defines a tray, said tray covering
      (a) the plurality of teeth including at least one tooth to be restored, and
      (b) the proximal soft tissues facial and lingual to the at least one tooth to be restored;
   separating the cured first curable material from the thermoformed sheet;
   forming an opening in the cured first curable material such that at least a portion of the at least one tooth to be restored is not covered by the first curable material when the first curable material is reseated on the final design model;
   reseating the first curable material with the opening onto the final design model;
   applying a second curable material onto the final design model of the patient's teeth and proximal soft tissues in the opening formed in the first curable material;
   covering the second curable material with the trimmed thermoformed sheet;
   curing the covered second curable material on the final design model under pressure to form the stent having a first portion formed of the first curable material, a second portion formed of the second curable material and a third portion formed of the thermoformed sheet; and
   removing the stent from the final design model to expose a mold cavity that defines contours of the final design model of the patient's teeth and proximal soft tissues.

14. The method according to claim 13 wherein the first curable material has an average thickness of about 0.5 mm to about 5 mm after curing.

15. The method according to claim 13 wherein the thermoformed sheet is more rigid than the second curable material after it has been cured.

16. The method according to claim 13 wherein both the thermoformed sheet and the second curable material, after curing, are sufficiently transmissive of light within the wavelength of 400 nm to 500 nm to cure a light-curable dental composition disposed in a portion of the mold cavity that defines contours of the at least one tooth to be restored.

17. The method according to claim 13 wherein the final design model of the patient's teeth and proximal soft tissues is formed by adding wax to a cast model of the patient's teeth and proximal soft tissues.

18. The method according to claim 13 wherein the final design model of the patient's teeth and proximal soft tissues is formed by removing material from a cast model of the patient's teeth and proximal soft tissues and adding wax to the cast model of the patient's teeth and proximal soft tissues.

* * * * *